US009040282B2

(12) United States Patent
Katz et al.

(10) Patent No.: US 9,040,282 B2
(45) Date of Patent: May 26, 2015

(54) PRODUCING DICARBOXYLIC ACIDS USING POLYKETIDE SYNTHASES

(71) Applicant: The Regents of the University of California, Oakland, CA (US)

(72) Inventors: Leonard Katz, Oakland, CA (US); Jeffrey L Fortman, San Francisco, CA (US); Jay D Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 61 days.

(21) Appl. No.: 14/038,488

(22) Filed: Sep. 26, 2013

(65) Prior Publication Data

US 2014/0030789 A1 Jan. 30, 2014

Related U.S. Application Data

(62) Division of application No. 12/922,204, filed as application No. PCT/US2009/038831 on Mar. 30, 2009, now Pat. No. 8,569,023.

(60) Provisional application No. 61/040,584, filed on Mar. 28, 2008.

(51) Int. Cl.

| | |
|---|---|
| ***C12N 1/20*** | (2006.01) |
| ***C12N 9/88*** | (2006.01) |
| ***C12N 9/10*** | (2006.01) |

(52) U.S. Cl.

CPC ................ *C12N 9/1029* (2013.01); *C12N 9/10* (2013.01)

(58) Field of Classification Search

CPC ................................ C12N 9/10; C12N 9/1029

USPC .............................................. 435/252.3, 232

See application file for complete search history.

(56) References Cited

U.S. PATENT DOCUMENTS

| | | | |
|---|---|---|---|
| 5,672,491 | A | 9/1997 | Khosla et al. |
| 5,712,146 | A | 1/1998 | Khosla et al. |
| 5,830,750 | A | 11/1998 | Khosla et al. |
| 5,843,718 | A | 12/1998 | Khosla et al. |
| 6,303,342 | B1 | 10/2001 | Julien et al. |
| 7,198,922 | B2 | 4/2007 | Leadlay et al. |

FOREIGN PATENT DOCUMENTS

| | | | |
|---|---|---|---|
| WO | WO 97/02358 | A1 | 1/1997 |
| WO | WO 98/49315 | A2 | 11/1998 |
| WO | WO 2009/121066 | | 6/2009 |

OTHER PUBLICATIONS

Bisang et al.; "A chain initiation factor common to both modular and aromatic polyketide synthases"; 1999, *Nature*, vol. 401, pp. 502-505.

Heathcote et al.; "Role of type II thioesterases: evidence for removal of short acyl chains produced by aberrant decarboxylation of chain extender units" 2001, *Chem Biol.*, vol. 8, No. 2, pp. 207-220.

Jacobsen et al.; "Precursor-Directed Biosynthesis of Erythromycin by Analogs by an Engineered Polyketide Synthase"; 1997, *Science*, vol. 277, pp. 367-369.

Erb et al.; "Synthesis of C5-dicarboxylic acids from C2-units involving crotonyl-CoA carboxylase/reductase: the ethylmalonyl-CoA pathway"; *Proc. Natl. Acad. Sci. U.S.A.*; 104(25):10631-10636 (Jun. 2007) Epub Jun. 4, 2007.

Supplementary European Search Report from EP 09724907.2. (3 pages), (2011).

*Primary Examiner* — Tekchand Saidha

(74) *Attorney, Agent, or Firm* — Kilpatrick Townsend & Stockton LLP

(57) ABSTRACT

The present invention provides for a polyketide synthase (PKS) capable of synthesizing a dicarboxylic acid (diacid). Such diacids include diketide-diacids and triketide-diacids. The invention includes recombinant nucleic acid encoding the PKS, and host cells comprising the PKS. The invention also includes methods for producing the diacids.

14 Claims, 7 Drawing Sheets

1

Nylon
2

3

4

5

6

Loading Modules

S1 S2

A B C D E F

Extender Modules

G H I J K L

M N O P

7

Novel polyamide

Novel polyester

8

Novel polyamide

Novel polyester

Pentanedioic acid

Heptanedioic acid

Spiramycin LM- nysmod5-eryTE

Spiramycin LM- nysMod5-epoMod5-eryTE

19

8

22

10 mAT ACP KS mmAT(S) ACP TE

34 mmAT ACP KS mmAT(*R*) KR(*R*) ACP TE

37 mAT ACP KS mAT KR DH ACP TE

483 mmAT ACP KS mmAT DH KR ACP/
KS mAT KR(*R*) ACP TE

117 mAT ACP KS mmAT(*R*) KR(*S*) ACP/
KS mAT KR(*S*) ACP TE

165 mmAT ACP KS mAT(*R*) KR(*S*) ACP/
KS mAT(*R*) KR(*S*) ACP TE

*n*-Butyric acid

Pentane-1,5-dioic acid [7]

PRODUCING DICARBOXYLIC ACIDS USING POLYKETIDE SYNTHASES

CROSS-REFERENCE TO RELATED APPLICATIONS

This application is a divisional of U.S. patent application Ser. No. 12/922,204, filed Sep. 28, 2010, which claims priority to U.S. Provisional Patent Application Ser. No. 61/040,584, filed Mar. 28, 2008. Each application is hereby incorporated by reference.

STATEMENT OF GOVERNMENTAL SUPPORT

This invention was made with government support under Contract No. DE-AC02-05CH11231 awarded by the U.S. Department of Energy and under Award No. 0540879 awarded by the National Science Foundation. The government has certain rights in the invention.

FIELD OF THE INVENTION

This invention relates generally to dicarboxylic acid production using polyketide synthases.

BACKGROUND OF THE INVENTION

Dicarboxylic acids (diacids) are important compounds that are used in the manufacture of commercial polymers (e.g. polyesters, polyurethanes). For example, see FIG. 1. The diacid adipic acid [1] is used mainly as a monomer in the production of nylon [2], a polyamide generated through the reaction of [1] with hexane-1,6-diamine. Polyesters (for use in fabrics and plastics of many compositions) are formed through the polymerization of terphthalic acid [3] and a dialcohol (diol) such as ethylene glycol (to make polyethylene terephalate [4]), propane diol (poly(1,3-propanediol terephthalate) [5]) or butanediol (poly(1,4-butanediolphthalate) [6]. Adipic acid is also used in the synthesis of various polyesters.

The large scale worldwide use of nylons and polyesters requires the production of approximately 8 billion metric tons of [1] and 15 billion metric tons of [3] annually. These diacids are themselves synthesized from starting materials extracted from petroleum. One means of reducing the large dependence on oil for the commercial production of polymers is to generate the diacids by a fermentation process involving the use of polyketide synthases.

SUMMARY OF THE INVENTION

The present invention provides for a polyketide synthase (PKS) capable of synthesizing a dicarboxylic acid (diacid). Such diacids include the diketide-diacids and triketide-diacids described in Tables 2A-F and Tables 3A-KK. Such diacids can also be polyketides of more than three ketide units, such as 4, 5, or 6 or more ketide units. Such diacids can also be polyketides of up to 8, 9 or 10 ketide units. Such diacids includes polyketides with functional groups comprising independently H, methyl, ethyl, hydroxyl, or carbonyl groups. In some embodiments, the diacid is a polyketide from 1, 2 or 3 to up to 4, 5, 6, 7, 8, 9, or 10 ketide units.

The present invention provides for a recombinant nucleic acid that encodes a polyketide synthase (PKS) of the present invention. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing a diacid, such as a diacid described in Tables 2A-F and Tables 3A-KK.

The present invention provides a method of producing a diacid, such as the diacids described in Tables 2A-F and Tables 3A-KK, comprising: providing a host cell of the present invention, and culturing said host cell in a suitable culture medium such that the diacid is produced. The method can further comprise isolating said diacid from the host cell and the culture medium. The method can further comprise reacting the diacid with a diamine to produce a nylon. Alternatively, the method can further comprise reacting the diacid with a dialcohol to produce a polyester.

The present invention provides for a composition comprising a diacid isolated from a host cell from which the diacid was produced, and trace residues and/or contaminants of the host cell.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
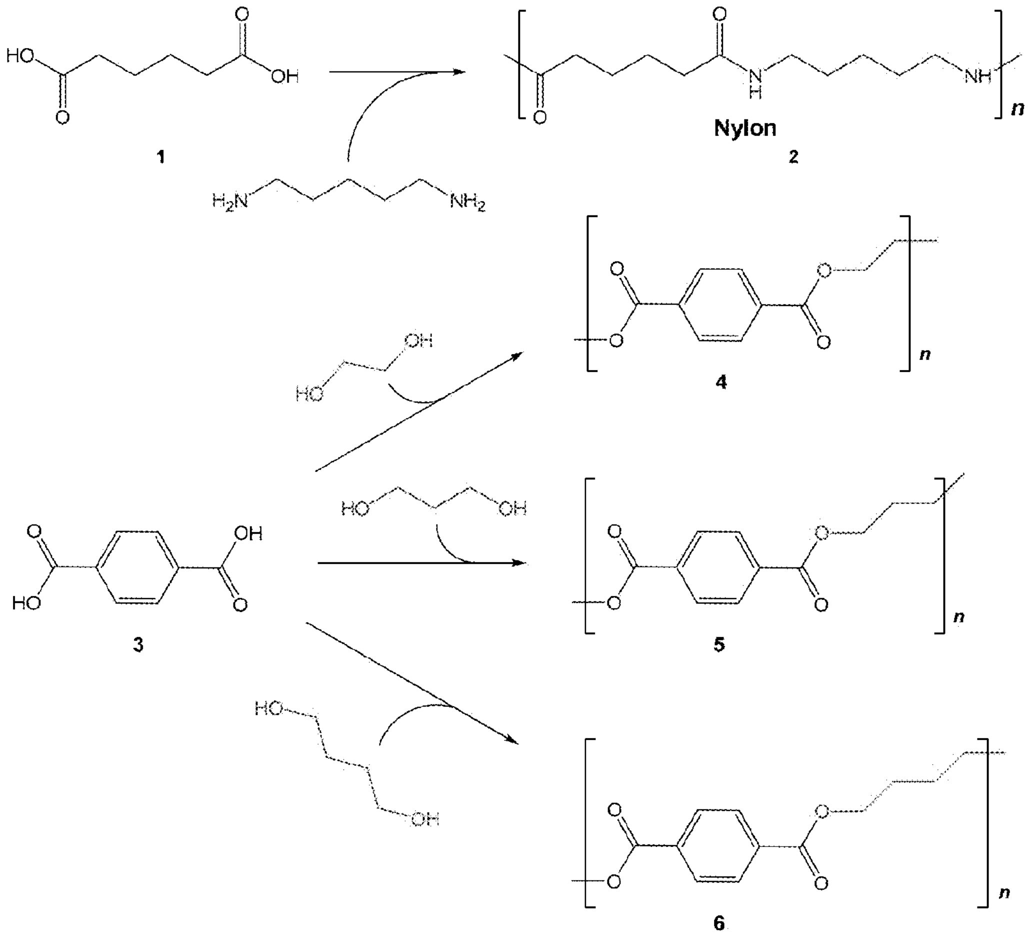
FIG. 1 shows the various reactions using diacids in the manufacture of commercial polymers (e.g. polyesters, polyurethanes). The diacid adipic acid [1] is used mainly as a monomer in the production of nylon [2], a polyamide generated through the reaction of [1] with hexane-1,6-diamine. Polyesters are formed through the polymerization of terphthalic acid [3] and a dialcohol (diol) such as ethylene glycol (to make polyethylene terephalate [4]), propane diol (poly(1,3-propanediol terephthalate) [5]) or butanediol (poly(1,4-butanediolphthalate) [6].

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a diacid" includes a plurality of such diacids, and so forth.

These and other objects, advantages, and features of the invention will become apparent to those persons skilled in the art upon reading the details of the invention as more fully described below.

Polyketide Synthases (PKS)

The present invention provides for a polyketide synthase (PKS) capable of synthesizing a diacid. Such diacids include the diketides and triketides described in Tables 2A-F and Tables 3A-KK. Such diacids can be polyketides of more than three ketide units, such as 4, 5, or 6 or more ketide units. The PKS can be in a host cell, or isolated or purified. The PKS can synthesize the diacid in vivo (in a host cell) or in vitro (in a cell extract or where all necessary chemical components or starting materials are provided). The present invention provides methods of producing the diacid using any of these in vivo or in vitro means. For example, a PKS capable of synthesizing diacid [9] comprises modules S1 and A (see Table 2A). For example, a PKS capable of synthesizing diacid [8] comprises modules S1, E and E (see Table 3A).

Figure 2:
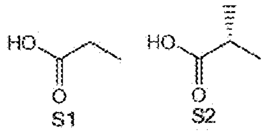
FIG. 2 shows types of modules employed and corresponding precursors utilized for incorporation into polyketide chains. Loading modules are designated S1 and S2. The remaining compounds represent the structures incorporated into the growing polyketide chain employing extender modules A-P. The dashed line indicates the C—C bond formed through Claisen condensation; atoms to the right of the bond and the C atom at the left of the dashed line represent the structures determined by the module employed. The R group represents the existing acyl chain prior to incorporation determined by the module.
Figure 2:
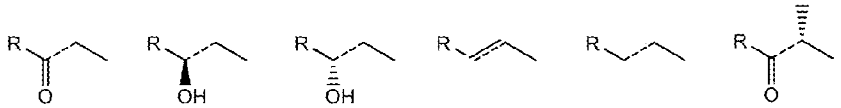
Figure 2:
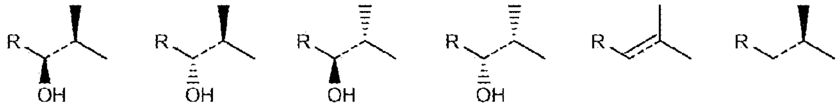
Figure 2:
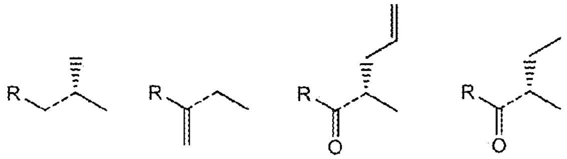

Polyketide synthases (PKS) employ short chain fatty acyl CoAs in Claisen condensation reactions to produce polyketides. Unlike fatty acid synthases which utilize acetyl CoA as the starter and malonyl CoA as the extender units, and use a single module iteratively to produce the nascent acyl chains, PKSs are composed of discrete modules, each catalyzing the chain growth of a single step. Modules can differ from each other in composition so that overall, a number of different starters (e.g. acetyl CoA, propionyl CoA) and extenders, some of which contain stereospecific methyl (or ethyl) side chains can be incorporated. In addition, PKS modules do not always reduce the 3-carbonyl formed from condensation but may leave it either unreduced (ketone), partially reduced (hydroxyl, 2,3-ene) or fully reduced (3-methylene). Many polyketide synthases employ malonyl CoA or [S]-2-methylmalonyl CoA as the starter for polyketide synthesis. In such cases the terminal carboxyl group is usually removed by a decarboxylase domain present at the N-terminus of the corresponding loading domain of the PKS. In summary, the structure (and chirality) of the α-carbon and β-carbonyl is determined by the module of the PKS employed in the synthesis of the growing chain at each particular step. Because of the correspondence between use of modules in the synthesis and the structure of the polyketide produced, it is possible to program the synthesis to produce a compound of desired structure by selection and genetic manipulation of polyketide synthases. Hence, the programming of PKSs to produce dicarboxylic acids can be accomplished by straightforward removal of the N-terminal decarboxylase domain from the loading module. FIG. 2 shows the various modules and the precursor utilized by each module for incorporation into the corresponding nascent acyl (polyketide) chain to give rise to the range of compounds of interest. Table 1 provides a PKS source for each module. Each PKS source is well-known to one skilled in the art is readily available. In addition, for each module taught in Table 1, there may be other modules from other PKS that can be used.

TABLE 1

PKS sources of the various modules.

| Module | PKS Source |
|---|---|
| S1 | Spiramycin PKS Loading Domain |
| S2 | Erythromycin PKS Loading Domain |
| A | Rifamycin PKS Module 2 |

TABLE 1-continued

PKS sources of the various modules.

| Module | PKS Source |
| --- | --- |
| B | Oligomycin PKS Module 1 |
| C | Spiramycin PKS Module 1 |
| D | Pikromycin PKS Module 2 |
| E | Oligomycin PKS Module 3 |
| F | Erythromycin PKS Module 3 |
| G | Oligomycin PKS Module 5 |
| H | Primaricin PKS Module 7 |
| I | Tylosin PKS Module 1 |
| J | Erythromycin PKS Module 1 |
| K | Avermectin PKS Module 7 |
| L | Rapamycin PKS Module 1 |
| M | Erythromycin PKS Module 4 |
| N | Pederin Module 2 |
| O | Ascomycin Module 4 |
| P | FK506 Module 4 |

Figure 9:
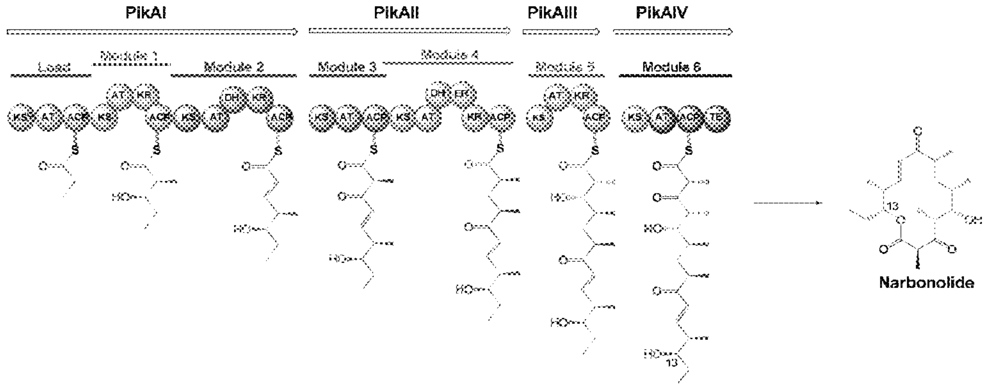
FIG. 9 shows the domain organization of the pik PKS and structures of proposed intermediates at the end of each condensation (and reduction) cycle (3). Linear polypeptides (Pik AI-AIV) are shown as open arrows; modules are indicated; domains are shown as spheres. Color-coding indicates the segment of the nascent polyketide chain corresponds to module and domains employing for programming Abbreviations: ACP, acyl carrier protein; AT, acyltransferase; DH; ER, enoylreductase; KR, β-ketoreductase; KS, β-keto acyl-ACP synthase; $KS^Q$; KS domain lacking condensation activity but maintaining decarboxylation activity; TE, thioesterase.

All extender modules carry the β-acyl ACP synthase (commonly called the ketosynthase or KS) domain, which conducts the decarboxylative condensation step between the extender and the growing polyketide chain, and the acyl carrier protein (ACP) domain that carries the growing acyl chain and presents it to the cognate reductive domains for reduction of the β-carbonyl. Modules can differ from each other in composition so that a number of different starter and extender units, some of which contain stereospecific side chains (e.g. methyl, ethyl, propylene) can be incorporated. The acyltransferase (AT) domain of each module determines the extender unit (e.g. malonyl CoA, methylmalonyl CoA, etc.) incorporated. In addition, PKS modules do not always reduce the β-carbonyl formed from condensation but may leave it either unreduced (ketone), partially reduced (hydroxyl, 2,3-ene) or fully reduced (3-methylene), as shown in FIG. 2. The ketoreductase (KR) domain reduces the ketone to the OH function (stereospecifically); the dehydratase (DH) domain removes water from the α and β carbons leaving an α,β trans-double bond; the enoylreductase (ER) domain reduces the double bond to a β-methylene center; the reductive state of the β-carbonyl, therefore, is determined by the presaence of functional reductive domains in the corresponding module. Less commonly, modules are found to contain an additional C-methylation domain (yielding an additional α-methyl side chain, as in epothilone). The makeup of the PKS, therefore, determines the choice of starter and extender acyl units incorporated, the extent of reduction at each condensation step, and the total number of units added to the chain. The wide diversity of structures of polyketides seen in nature is attributed to the diversity in PKS compositions. The PKS-directed synthesis of the aglycone component (narbonolide) of the antibiotic pikromycin is shown in FIG. 9. The pik PKS employs 6 modules (the loading domain is at the N-terminus of module 1); the loading domain and modules 1, 3, 4, 5, & 6 employs the precursor [S]-2-methylmalonyl CoA, module 2 uses malonyl CoA. (After incorporation, however, three of the side chains are inverted through a process not as yet fully understood.) The various degrees of reduction after each condensation cycle are determined by the presence of the corresponding reduction domains in each module. The cyclic nature of the product of the PKS is due to the TE domain-catalyzed nucleophilic attack of the OH generated after the first condensation cycle on the terminal thioester bond at ACP6. The structure of the polyketide narbonolide, therefore, is programmed by the pik PKS.

The PKS Loading Domain and Formation of Diacids.

Though virtually all polyketides appear to start with a short chain carboxylic acid (e.g. acetyl CoA or propionyl CoA), in reality, most of the polyketide synthases employ malonyl CoA or [S]-2-methylmalonyl CoA as the starter for polyketide synthesis. In such cases, as shown in FIG. 9 for the pik PKS, the terminal carboxyl group at the beginning of acyl chain growth is removed by a decarboxylase domain present at the N-terminus of the corresponding loading domain of the PKS, designated $KS^Q$. Termination of synthesis and release of the polyketide chain from the PKS normally results in the generation of a free carboxylic acid (if the acceptor of chain release is water) or, more commonly, a lactone (where the acceptor is an OH group internal to the chain). Failure to remove the carboxyl group at the initiation of chain growth would result in the generation of a diacid (if the opportunity for lactonization were prevented). This can be accomplished by removal of the $KS^Q$ domain from the loading domain of the PKS.

Figure 10:
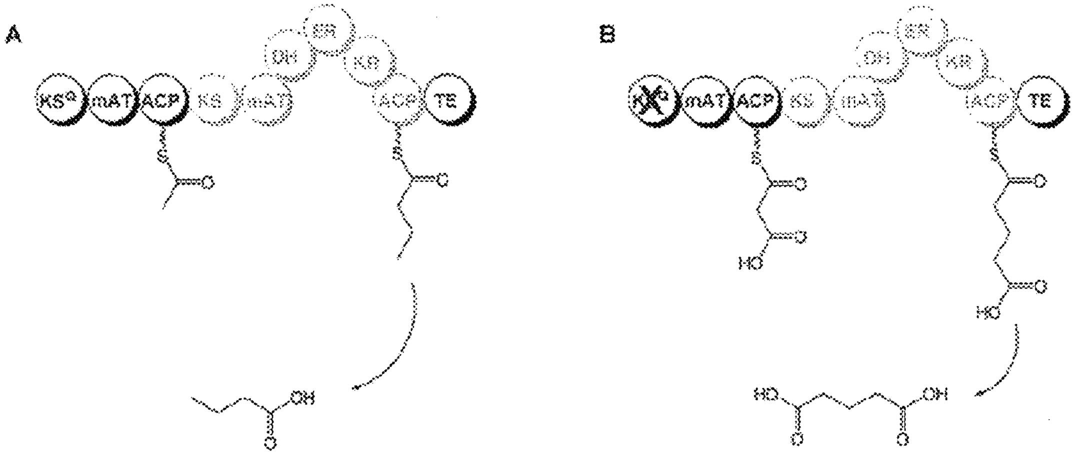
FIG. 10. A. Hybrid PKS composed of a loading domain containing a functional $KS^Q$ domain (blue), a single extender module (orange), and a TE domain (black), producing butyric acid. B. The same PKS as in A but lacking a functional $KS^Q$ domain, producing pentanedioic acid. Abbreviations as in FIG. 9 except that mAT indicates a malonyl-specific AT domain. The color scheme is used to indicate that the loading domain, module 1, and the thiesterase domain may come from different sources

An example is shown in FIG. 10, which shows a simple PKS composed of a loading domain, a single extender module capable of full reduction of the β-carbonyl group and a TE domain; the AT domains utilize malonyl CoA as starter and extender units. The loading domain incorporates malonyl CoA but decarboxylates it leaving the two carbon acetyl-ACP moiety. Decarboxylative condensation by module 1 with a second malonyl CoA and full reduction of the β-carbonyl group generated, followed by chain release generates n-butyric acid, a 4-carbon molecule. If the $KS^Q$ domain of the constructed PKS were removed, the malonyl-ACP moiety produced by the loading domain would not be decarboxylated; subsequent condensation, reduction and chain termination would release the 5-carbon diacid, pentane-1,5-dioic acid [7]. If a second extender module capable of incorporation of malonyl CoA and full β-carbonyl reduction were added to the $KS^Q$-deleted PKS, the resulting compound would be a 7-carbon diacid (hepatane-1,7-dioic acid). Thus, the 6-carbon straight chain diacid (adipic acid) cannot be made by PKS engineering described here. As will be described below, however, it is possible to engineer PKSs to make a 6-carbon branched chain (2-methylpentane) diacid.

Engineering Polyketide Synthases

The present invention provides for a recombinant nucleic acid that encodes a polyketide synthase (PKS) of the present invention. The recombinant nucleic acid can be a double-stranded or single-stranded DNA, or RNA. The recombinant nucleic acid can encode an open reading frame (ORF) of the PKS of the present invention. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is a plasmid. The present invention also provides for a vector or expression vector comprising a recombinant nucleic acid of the present invention.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

As noted, particularly useful control sequences are those which themselves, or with suitable regulatory systems, activate expression during transition from growth to stationary phase in the vegetative mycelium. Illustrative control sequences, vectors, and host cells of these types include the modified *S. coelicolor* CH999 and vectors described in PCT publication no. WO 96/40968 and similar strains of *S. lividans*. See U.S. Pat. Nos. 5,672,491; 5,830,750; 5,843,718; and 6,177,262, each of which is hereby incorporated by reference. Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

The present invention provides for a host cell comprising any of the recombinant nucleic acid and/or PKS of the present invention. In some embodiments, the host cell, when cultured, is capable of producing a diacid described in Tables 2A-F and Tables 3A-KK. The host cell can be a eukaryotic or a prokaryotic cell. Suitable eukaryotic cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable prokaryotic cells include *Escherichia coli* or *Streptomyces* species.

Of the more than thirty PKSs examined, the correspondence between use of modules in the biosynthesis and the structure of the polyketide produced is fully understood both at the level of the protein sequence of the PKS and the DNA sequence of the corresponding genes. The programming of modules into polyketide structure can be identified by sequence determination. It is possible to clone (or synthesize) DNA sequences corresponding to desired modules and transfer them as fully functioning units to heterologous, otherwise non-polyketide producing hosts such as *E. coli* (B. A. Pfeifer, S. J. Admiraal, H. Gramajo, D. E. Cane, C. Khosla, *Science* 291, 1790 (2001); hereby incorporated by reference) and *Streptomyces* (C. M. Kao, L. Katz, C. Khosla, *Science* 265, 509 (1994); hereby incorporated by reference). Additional genes employed for polyketide biosynthesis have also been identified. Genes that determine phosphopantetheine:protein transferase (PPTase) that transfer the 4-phosphopantetheine co-factor of the ACP domains, commonly present in polyketide producing hosts, have been cloned in *E. coli* and other hosts (K. I. Weissman, H. Hong, M. Oliynyk, A. P. Siskos, P. F. Leadlay, *Chembiochem* 5, 116 (2004); hereby incorporated by reference). Moreover, genes for the production of precursors such as methylmalonyl CoA and ethylmalonyl CoA have also been identified and cloned in heterologous hosts. It is also possible to re-program polyketide biosynthesis to produce a compound of desired structure by either genetic manipulation of a single PKS or by construction of a hybrid PKS composed of modules from two or more sources (K. J. Weissman, H. Hong, M. Oliynyk, A. P. Siskos, P. F. Leadlay, *Chembiochem* 5, 116 (2004); hereby incorporated by reference). Hence, the programming of PKSs to produce diacids of desired structure can be accomplished by straightforward removal of the N-terminal decarboxylase domain from the loading module followed by fusion of the altered loading domain with one or more extender modules as shown in FIG. 10.

Recombinant methods for manipulating modular PKS genes to make the PKSs of the present invention are described in U.S. Pat. Nos. 5,672,491; 5,843,718; 5,830,750; 5,712,146; and 6,303,342; and in PCT publication nos. WO 98/49315 and WO 97/02358; hereby incorporated by reference. A number of genetic engineering strategies have been used with various PKSs to demonstrate that the structures of polyketides can be manipulated to produce novel polyketides (see the patent publications referenced supra and Hutchinson, 1998, Curr Opin Microbiol. 1:319-329, and Baltz, 1998, Trends Microbiol. 6:76-83; hereby incorporated by reference). In some embodiment, the components of the hybrid PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication no. WO 00/47724, hereby incorporated by reference.

Figure 4:
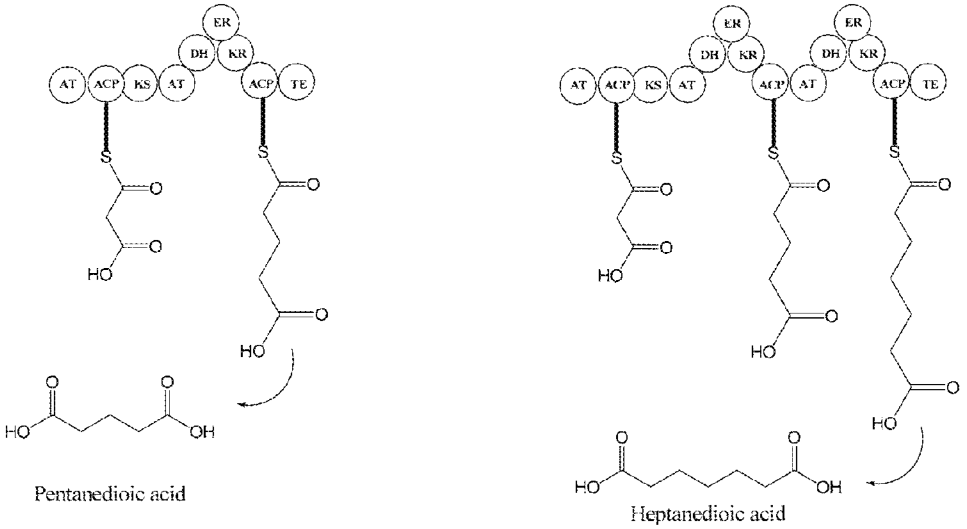
FIG. 4 shows two example of the enzymatic PKS systems use to biosynthesize-derived diacids.

The genetic constructs will employ an inactivation or deletion of the $KS^{Q}$ domains of the loading module so that the pendent acid functionality will be retained. The loading domain will be fused to one or more extender modules. The final module will be fused with a thioesterase (TE) domain. For example, the loading domain (LM) from the spiramycin PKS in *Streptomyces ambofaciens* can be fused to module 5 of the nystatin (nysMod5) PKS from *Streptomyces noursei* and the TE domain from the erythromycin PKS (eryTE) from *Saccharopolyspora erythraea* to yield a hybrid polyketide synthase enzyme that would produce pentanedioic (glutaric acid) (FIG. 4). The insertion of module 5 from the epothilone PKS (epoMod5) from *Sorangium cellulosum* between nysMod5 and eryTE would yield heptanedioc acid (FIG. 4).

There is a publication that suggests that the ery TE is capable of releasing free acids in our system. This is an in vitro analysis, but this property is expected to transfer to an in vivo system. Another option to be considered is the use of the thioesterase MonCII from the monensin pathway in *Streptomyces cinnamonensis*. This enzyme has been implicated in the release of the linear free acid from the PKS megasynthase.

The vast number of polyketide pathways that have been elucidated provide a host of different options to produce these diacids as well as the large number of derivatives shown in Tables 2 and 3. While the products can be vastly different in size and functionality, all employ virtually the same strategy for biosynthesis. The exact interfaces between non-cognate enzyme partners will be determined on a case-by-case basis. ACP-linker-KS and ACP-linker-TE regions from the proteins of interest will be aligned to examine the least disruptive fusion point for the hybrid synthase. Genetic constructions will employ sequence and ligation independent cloning (SLIC) so as to eliminate the incorporation of genetic "scarring".

A partial list of sources of PKS sequences that can be used in making the PKSs of the present invention, for illustration and not limitation, includes Ambruticin (U.S. Pat. No. 7,332,576); Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FR0008) (Hu et al., 1994, Mol. Microbiol. 14: 163-72); Epothilone (U.S. Pat. No. 6,303,342); Erythromycin (WO 93/13663; U.S. Pat. No. 5,824,513; Donadio et al., 1991, Science 252:675-79; Cortes et al., 1990, Nature 348:176-8); FK506 (Motamedi et al., 1998, Eur. J. Biochem. 256:528-34; Motamedi et al., 1997, Eur. J. Biochem. 244:74-80); FK520 or ascomycin (U.S. Pat. No. 6,503,737; see also Nielsen et al., 1991, Biochem. 30:5789-96); Jerangolid (U.S. Pat. No. 7,285,405); Leptomycin (U.S. Pat. No. 7,288,396); Lovastatin (U.S. Pat. No. 5,744,350); Nemadectin (MacNeil et al., 1993, supra); Niddamycin (Kakavas et al., 1997, J. Bacteriol. 179:7515-22); Oleandomycin (Swan et al., 1994, Mol. Gen. Genet. 242:358-62; U.S. Pat. No. 6,388,099; Olano et al., 1998, Mol. Gen. Genet. 259:299-308); Pederin (PCT publication no. WO 2003/044186); Pikromycin (Xue et al., 2000, Gene 245:203-211); Pimaricin (PCT publication no. WO 2000/077222); Platenolide (EP Pat. App. 791,656); Rapamycin (Schwecke et al., 1995, Proc. Natl. Acad. Sci. USA 92:7839-43); Aparicio et al., 1996, Gene 169:9-16); Rifamycin (August et al., 1998, Chemistry & Biology, 5: 69-79); Soraphen (U.S. Pat. No. 5,716,849; Schupp et al., 1995, J. Bacteriology 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences are readily available to one skilled in the art, or remain to be discovered and characterized, but will be available to those of skill (e.g., by reference to GenBank). Each of the references cited is hereby specifically and individually incorporated by reference.

Complex polyketides comprise a large class of natural products that are synthesized in bacteria (mainly members actinomycete family; e.g. *Streptomyces*), fungi and plants. Polyketides form the aglycone component of a large number of clinically important drugs, such as antibiotics (e.g. erythromycin, tylosin), antifungal agents (e.g. nystatin), anticancer agents (e.g. epothilone), immunosuppressives (e.g. rapamycin), etc. Though these compounds do not resemble each other either in their structure or their mode of action, they share a common basis for their biosynthesis, which is carried out by a group of enzymes designated polyketide synthases.

Diacids and Triacids Produced by PKSs

The present invention provides a method of producing a diacid, such as a diacid described in Tables 2A-F and Tables 3A-KK, comprising: providing a host cell of the present invention, and culturing said host cell in a suitable culture medium such that a diacid is produced. The method can further comprise isolating said diacid from the host cell and the culture medium. The method can further comprise reacting the diacid with a diamine to produce a nylon. A suitable diamine is an alkane diamine, such as hexane-1,6-diamine Alternatively, the method can further comprise reacting the diacid with a dialcohol to produce a polyester. A suitable dialcohol is an alkane diol, such as ethylene glycol, propane diol, or butanediol. A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 20020192767 and 20020045220; hereby incorporated by reference.

The present invention provides for a composition comprising a diacid isolated from a host cell from which the diacid was produced, and trace residues and/or contaminants of the host cell.

Adipic acid is a six carbon chain fully reduced symmetrical aliphatic compound with no side chains, hence no chiral centers. Only odd numbered chain length dicarboxylates can be generated by PKSs. Five-membered chains are formed from the condensation of a starter acyl unit and two extender acyl units. Regardless of the state of reduction of the compound, these are designed diketides and require a loading module and one extender module for their syntheses. Seven-membered chains, triketides, are formed from the condensation of a starter and two extender units, and employ a loading module and two extender modules. Side chains (methyl, allyl, hydroxyl) may be incorporated or formed, depending on the modules employed. Symmetric compounds with non-chiral centers most similar in structure to adipic acid that can be produced by programmed PKSs are the diketide n-pentanedioic (glutaric) acid [7] and the triketide n-heptanedoic acid [8]. These compounds are produced through the construction of a

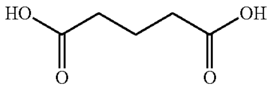

7

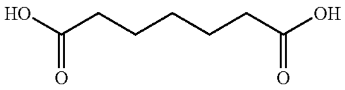

Figure 3:
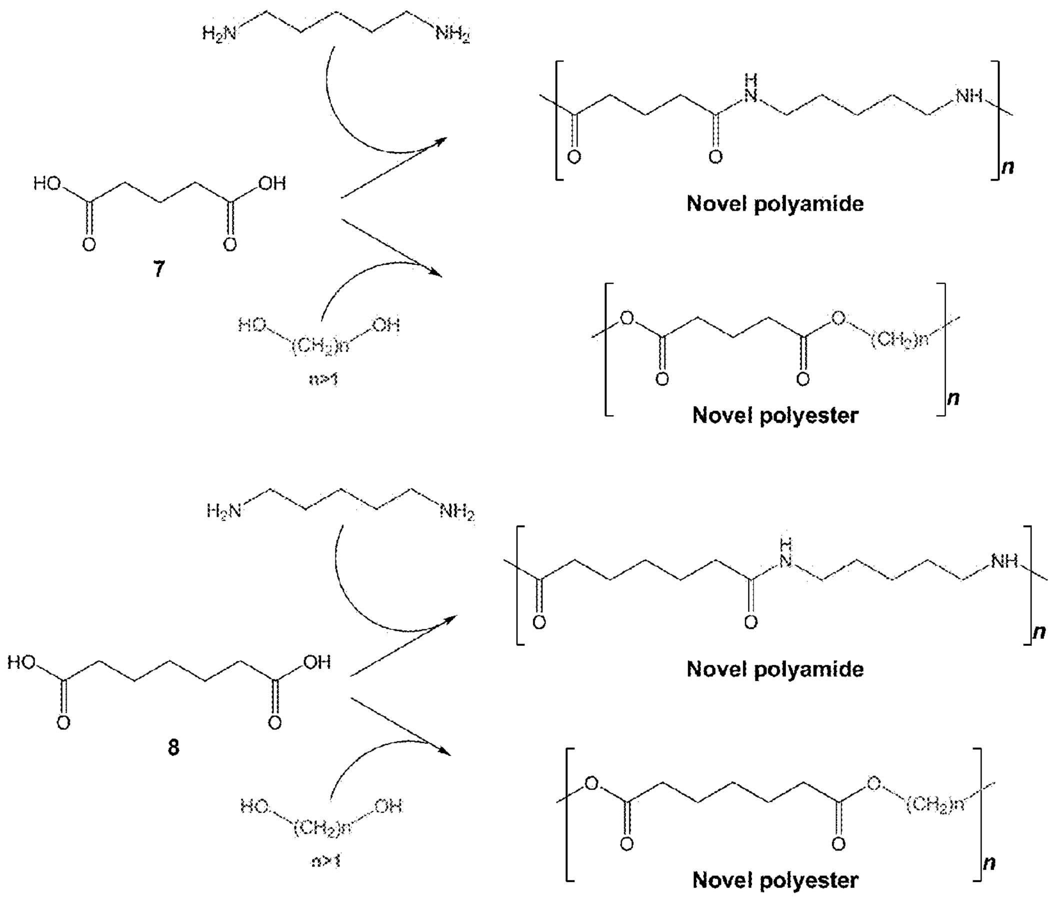
FIG. 3 shows a scheme for making novel polyamides or novel polyesters.

8 polyketide synthase composed of loading module S1 and extender module E [7] or S1 and two E extender modules [8] (FIG. 2). These molecules can be used as replacements for adipic acid or other diacids to make novel polyamides or novel polyesters as shown in the scheme in FIG. 3. All other diacids produced as di- and triketides by PKSs will be asymmetric. They will contain one or more double bonds or hydroxyl groups and/or one or more methyl side chains, hence they will give rise to a mixture of compounds upon polymerization. Asymmetric mixtures currently have substantial use as low profile additives in the production of adhesive compositions used in the manufacture of a variety of plastics.

Starting with S1 or S2, and employing any of the extender modules shown in FIG. 2 to construct PKSs, 32 diketide-diacids and 512 tri-ketide-diacids can be produced. Considering stereochemistry, each would be chemically distinct and unique. All but compound [7] would be asymmetric. The rigidity of the backbone is enhanced by the presence of double bonds and side chains. The diketides possible are shown in Tables 2A-F and the triketides possible are shown in Table 3A-KK.

Tables 2A-F. Possible diketide-diacids produced from use of modules shown in FIG. 2

TABLE 2A

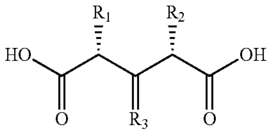

| | | | | Modules | |
|---|---|---|---|---|---|
| | $R_1$ | $R_2$ | $R_3$ | LM | Mod1 |
| 9 | H | H | O | S1 | A |
| 10 | H | $CH_3$ | O | S1 | F |
| 11 | H | $(CH_2)_3$ | O | S1 | O |
| 12 | H | $CH_2CH_3$ | O | S1 | P |
| 13 | H | H | $CH_2$ | S1 | N |
| 14 | $CH_3$ | H | O | S2 | A |
| 15 | $CH_3$ | $CH_3$ | O | S2 | F |
| 16 | $CH_3$ | $(CH_2)_3$ | O | S2 | O |
| 17 | $CH_3$ | H | $CH_2$ | S2 | N |
| 18 | $CH_3$ | $CH_2CH_3$ | O | S2 | P |

TABLE 2D

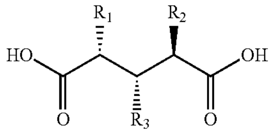

| | | | | Modules | |
|---|---|---|---|---|---|
| | $R_1$ | $R_2$ | $R_3$ | LM | Mod1 |
| 31 | H | $CH_3$ | H | S1 | L |
| 32 | H | $CH_3$ | OH | S1 | H |
| 33 | $CH_3$ | $CH_3$ | H | S2 | L |
| 34 | $CH_3$ | $CH_3$ | OH | S2 | H |

TABLE 2B

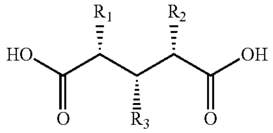

| | | | | Modules | |
|---|---|---|---|---|---|
| | $R_1$ | $R_2$ | $R_3$ | LM | Mod1 |
| 7 | H | H | H | S1 | E |
| 19 | H | H | OH | S1 | C |
| 20 | H | $CH_3$ | H | S1 | M |
| 21 | H | $CH_3$ | OH | S1 | J |
| 22 | $CH_3$ | H | H | S2 | E |
| 23 | $CH_3$ | H | OH | S2 | C |
| 24 | $CH_3$ | $CH_3$ | H | S2 | M |
| 25 | $CH_3$ | $CH_3$ | OH | S2 | J |

TABLE 2E

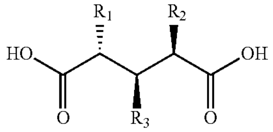

| | | | | Modules | |
|---|---|---|---|---|---|
| | $R_1$ | $R_2$ | $R_3$ | LM | Mod1 |
| 35 | H | $CH_3$ | OH | S1 | G |
| 36 | $CH_3$ | $CH_3$ | OH | S2 | G |

TABLE 2C

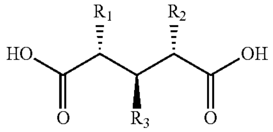

| | | | | Modules | |
|---|---|---|---|---|---|
| | $R_1$ | $R_2$ | $R_3$ | LM | Mod1 |
| 26 | H | H | OH | S1 | B |
| 27 | H | $CH_3$ | OH | S1 | I |
| 28 | $CH_3$ | H | OH | S2 | B |
| 30 | $CH_3$ | $CH_3$ | OH | S2 | I |

TABLE 2F

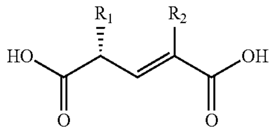

| | | | Modules | |
|---|---|---|---|---|
| | $R_1$ | $R_2$ | LM | Mod1 |
| 37 | H | H | S1 | D |
| 38 | H | $CH_3$ | S1 | K |
| 39 | $CH_3$ | H | S2 | D |
| 40 | $CH_3$ | $CH_3$ | S2 | K |

Tables 3A-KK. Possible triketide-diacids produced from use of modules shown in FIG. 2.

TABLE 3A

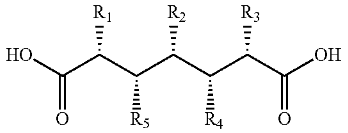

| | | | | | | Modules | | |
|---|---|---|---|---|---|---|---|---|
| | $R_1$ | $R_2$ | $R_3$ | $R_4$ | $R_5$ | LM | Mod1 | Mod2 |
| 8 | H | H | H | H | H | S1 | E | E |
| 41 | H | H | H | OH | H | S1 | E | C |
| 42 | H | H | H | H | OH | S1 | C | E |
| 43 | H | H | H | OH | OH | S1 | C | C |
| 44 | H | H | $CH_3$ | H | H | S1 | E | M |
| 45 | H | H | $CH_3$ | OH | H | S1 | E | J |
| 46 | H | H | $CH_3$ | H | OH | S1 | C | M |
| 47 | H | H | $CH_3$ | OH | OH | S1 | C | J |
| 48 | H | $CH_3$ | H | H | H | S1 | M | E |
| 49 | H | $CH_3$ | H | OH | H | S1 | M | C |
| 50 | H | $CH_3$ | H | H | OH | S1 | J | E |
| 51 | H | $CH_3$ | H | OH | OH | S1 | J | C |
| 52 | H | $CH_3$ | $CH_3$ | H | H | S1 | M | M |
| 53 | H | $CH_3$ | $CH_3$ | OH | H | S1 | M | J |
| 54 | H | $CH_3$ | $CH_3$ | H | OH | S1 | J | M |
| 55 | H | $CH_3$ | $CH_3$ | OH | OH | S1 | J | J |
| 56 | $CH_3$ | H | H | H | H | S2 | E | E |
| 57 | $CH_3$ | H | H | OH | H | S2 | E | C |
| 58 | $CH_3$ | H | H | H | OH | S2 | C | E |
| 59 | $CH_3$ | H | H | OH | OH | S2 | C | C |
| 60 | $CH_3$ | H | $CH_3$ | H | H | S2 | E | M |
| 61 | $CH_3$ | H | $CH_3$ | OH | H | S2 | E | J |
| 62 | $CH_3$ | H | $CH_3$ | H | OH | S2 | M | C |
| 63 | $CH_3$ | H | $CH_3$ | OH | OH | S2 | C | J |
| 64 | $CH_3$ | $CH_3$ | H | H | H | S2 | M | E |
| 65 | $CH_3$ | $CH_3$ | H | OH | H | S2 | M | C |
| 66 | $CH_3$ | $CH_3$ | H | H | OH | S2 | J | E |
| 67 | $CH_3$ | $CH_3$ | H | OH | OH | S2 | J | C |
| 68 | $CH_3$ | $CH_3$ | $CH_3$ | H | H | S2 | M | M |
| 69 | $CH_3$ | $CH_3$ | $CH_3$ | OH | H | S2 | M | J |
| 70 | $CH_3$ | $CH_3$ | $CH_3$ | H | OH | S2 | J | M |
| 71 | $CH_3$ | $CH_3$ | $CH_3$ | OH | OH | S2 | J | J |

TABLE 3B

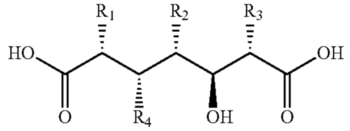

| | | | | | | Modules | |
|---|---|---|---|---|---|---|---|
| | $R_1$ | $R_2$ | $R_3$ | $R_4$ | LM | Mod1 | Mod2 |
| 72 | H | H | H | H | S1 | E | B |
| 73 | H | H | $CH_3$ | H | S1 | E | I |
| 74 | H | $CH_3$ | H | H | S1 | M | B |
| 75 | H | $CH_3$ | $CH_3$ | H | S1 | M | I |
| 76 | H | H | H | OH | S1 | G | B |
| 77 | H | H | $CH_3$ | OH | S1 | C | I |
| 78 | H | $CH_3$ | H | OH | S1 | J | B |
| 79 | H | $CH_3$ | $CH_3$ | OH | S1 | J | I |
| 80 | $CH_3$ | H | H | H | S2 | E | B |
| 81 | $CH_3$ | H | $CH_3$ | H | S2 | E | I |
| 82 | $CH_3$ | $CH_3$ | H | H | S2 | M | B |
| 83 | $CH_3$ | $CH_3$ | $CH_3$ | H | S2 | M | I |
| 84 | $CH_3$ | H | H | OH | S2 | C | B |
| 85 | $CH_3$ | H | $CH_3$ | OH | S2 | C | I |
| 86 | $CH_3$ | $CH_3$ | H | OH | S2 | J | B |
| 87 | $CH_3$ | $CH_3$ | $CH_3$ | OH | S2 | J | I |

TABLE 3C

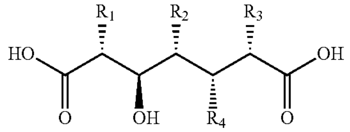

| | | | | | | Modules | |
|---|---|---|---|---|---|---|---|
| | $R_1$ | $R_2$ | $R_3$ | $R_4$ | LM | Mod1 | Mod2 |
| 88 | H | H | H | H | S1 | B | E |
| 89 | H | H | $CH_3$ | H | S1 | B | M |
| 90 | H | H | H | OH | S1 | B | C |
| 91 | H | H | $CH_3$ | OH | S1 | B | J |
| 92 | H | $CH_3$ | H | H | S1 | I | E |
| 93 | H | $CH_3$ | $CH_3$ | H | S1 | I | M |
| 94 | H | $CH_3$ | H | OH | S1 | I | C |
| 95 | H | $CH_3$ | $CH_3$ | OH | S1 | I | J |
| 96 | $CH_3$ | H | H | H | S2 | B | E |
| 97 | $CH_3$ | H | $CH_3$ | H | S2 | B | M |
| 98 | $CH_3$ | H | H | OH | S2 | B | C |
| 99 | $CH_3$ | H | $CH_3$ | OH | S2 | B | J |
| 100 | $CH_3$ | $CH_3$ | H | H | S2 | I | E |
| 101 | $CH_3$ | $CH_3$ | $CH_3$ | H | S2 | I | M |
| 102 | $CH_3$ | $CH_3$ | H | OH | S2 | I | C |
| 103 | $CH_3$ | $CH_3$ | $CH_3$ | OH | S2 | I | J |

TABLE 3D

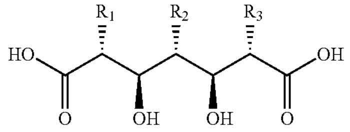

| | | | | | Modules | |
|---|---|---|---|---|---|---|
| | $R_1$ | $R_2$ | $R_3$ | LM | Mod1 | Mod2 |
| 104 | H | H | H | S1 | B | B |
| 105 | H | H | $CH_3$ | S1 | B | I |
| 106 | H | $CH_3$ | H | S1 | I | B |
| 107 | H | $CH_3$ | $CH_3$ | S1 | B | I |

TABLE 3D-continued

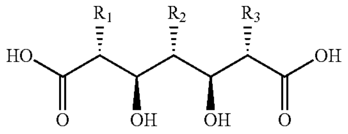

| | | | | Modules | | |
|---|---|---|---|---|---|---|
| | $R_1$ | $R_2$ | $R_3$ | LM | Mod1 | Mod2 |
| 108 | $CH_3$ | H | H | S2 | B | B |
| 109 | $CH_3$ | H | $CH_3$ | S2 | B | I |
| 110 | $CH_3$ | $CH_3$ | H | S2 | I | B |
| 111 | $CH_3$ | $CH_3$ | $CH_3$ | S2 | I | I |

TABLE 3E

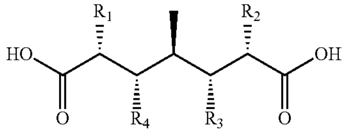

| | | | | | Modules | | |
|---|---|---|---|---|---|---|---|
| | $R_1$ | $R_2$ | $R_3$ | $R_4$ | LM | Mod1 | Mod2 |
| 112 | H | H | H | H | S1 | L | E |
| 113 | H | H | OH | H | S1 | L | C |
| 114 | H | $CH_3$ | H | H | S1 | L | M |
| 115 | H | $CH_3$ | OH | H | S1 | L | J |
| 116 | H | H | H | OH | S1 | H | E |
| 117 | H | H | OH | OH | S1 | H | C |
| 118 | H | $CH_3$ | H | OH | S1 | H | M |
| 119 | H | $CH_3$ | OH | OH | S1 | H | J |
| 120 | $CH_3$ | H | H | H | S2 | L | E |
| 121 | $CH_3$ | H | OH | H | S2 | L | C |
| 122 | $CH_3$ | $CH_3$ | H | H | S2 | L | M |
| 123 | $CH_3$ | $CH_3$ | OH | H | S2 | L | J |
| 124 | $CH_3$ | H | H | OH | S2 | H | E |
| 125 | $CH_3$ | H | OH | OH | S2 | H | C |
| 126 | $CH_3$ | $CH_3$ | H | OH | S2 | H | M |
| 127 | $CH_3$ | $CH_3$ | OH | OH | S2 | H | J |

TABLE 3F

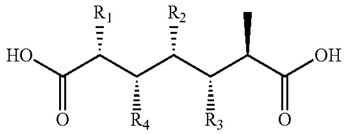

| | | | | | Modules | | |
|---|---|---|---|---|---|---|---|
| | $R_1$ | $R_2$ | $R_3$ | $R_4$ | LM | Mod1 | Mod2 |
| 128 | H | H | H | H | S1 | E | L |
| 129 | H | H | OH | H | S1 | E | H |
| 130 | H | H | H | OH | S1 | C | L |
| 131 | H | H | OH | OH | S1 | C | H |
| 132 | H | $CH_3$ | H | H | S1 | M | L |
| 133 | H | $CH_3$ | OH | H | S1 | M | H |
| 134 | H | $CH_3$ | H | OH | S1 | J | L |
| 135 | H | $CH_3$ | OH | OH | S1 | J | H |
| 136 | $CH_3$ | H | H | H | S2 | E | L |
| 137 | $CH_3$ | H | OH | H | S2 | E | H |
| 138 | $CH_3$ | H | H | OH | S2 | C | L |
| 139 | $CH_3$ | H | OH | OH | S2 | C | H |
| 140 | $CH_3$ | $CH_3$ | H | H | S2 | M | L |
| 141 | $CH_3$ | $CH_3$ | OH | H | S2 | M | H |
| 142 | $CH_3$ | $CH_3$ | H | OH | S2 | J | L |
| 143 | $CH_3$ | $CH_3$ | OH | OH | S2 | J | H |

TABLE 3G

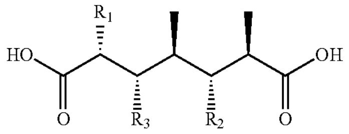

| | | | | | Modules | |
|---|---|---|---|---|---|---|
| | $R_1$ | $R_2$ | $R_3$ | LM | Mod1 | Mod2 |
| 144 | H | H | H | S1 | L | L |
| 145 | H | OH | H | S1 | L | H |
| 146 | H | H | OH | S1 | H | L |
| 147 | H | OH | OH | S1 | H | H |
| 148 | $CH_3$ | H | H | S2 | L | L |
| 149 | $CH_3$ | OH | H | S2 | L | H |
| 150 | $CH_3$ | H | OH | S2 | H | L |
| 151 | $CH_3$ | OH | OH | S2 | H | H |

TABLE 3H

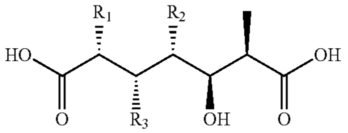

| | | | | | Modules | |
|---|---|---|---|---|---|---|
| | $R_1$ | $R_2$ | $R_3$ | LM | Mod1 | Mod2 |
| 152 | H | H | H | S1 | E | G |
| 153 | H | H | OH | S1 | C | G |
| 154 | H | $CH_3$ | H | S1 | M | G |
| 155 | H | $CH_3$ | OH | S1 | J | G |
| 156 | $CH_3$ | H | H | S2 | E | G |
| 157 | $CH_3$ | H | OH | S2 | C | G |
| 158 | $CH_3$ | $CH_3$ | H | S2 | M | G |
| 159 | $CH_3$ | $CH_3$ | OH | S2 | J | G |

TABLE 3I

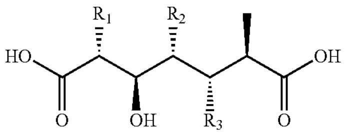

| | | | | | Modules | |
|---|---|---|---|---|---|---|
| | $R_1$ | $R_2$ | $R_3$ | LM | Mod1 | Mod2 |
| 160 | H | H | H | S1 | B | L |
| 161 | H | H | OH | S1 | B | H |
| 162 | H | $CH_3$ | H | S1 | I | L |
| 163 | H | $CH_3$ | OH | S1 | I | H |
| 164 | $CH_3$ | H | H | S2 | B | L |
| 165 | $CH_3$ | H | OH | S2 | B | H |
| 168 | $CH_3$ | $CH_3$ | H | S2 | I | L |
| 167 | $CH_3$ | $CH_3$ | OH | S2 | I | H |

TABLE 3J

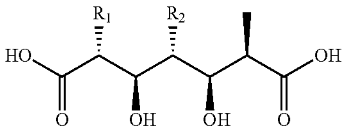

| | | | Modules | | |
|---|---|---|---|---|---|
| | $R_1$ | $R_2$ | LM | Mod1 | Mod2 |
| 168 | H | H | S1 | B | G |
| 169 | H | $CH_3$ | S1 | I | G |
| 170 | $CH_3$ | H | S2 | B | G |
| 171 | $CH_3$ | $CH_3$ | S2 | I | G |

TABLE 3K

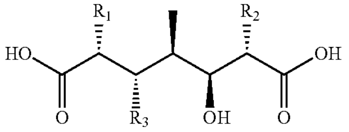

| | | | | Modules | | |
|---|---|---|---|---|---|---|
| | $R_1$ | $R_2$ | $R_3$ | LM | Mod1 | Mod2 |
| 172 | H | H | H | S1 | L | B |
| 173 | H | $CH_3$ | H | S1 | L | I |
| 174 | H | H | OH | S1 | H | B |
| 175 | H | $CH_3$ | OH | S1 | H | I |
| 176 | $CH_3$ | H | H | S2 | L | B |
| 177 | $CH_3$ | $CH_3$ | H | S2 | L | I |
| 178 | $CH_3$ | H | OH | S2 | H | B |
| 179 | $CH_3$ | $CH_3$ | OH | S2 | H | I |

TABLE 3L

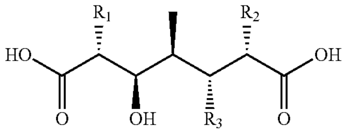

| | | | | Modules | | |
|---|---|---|---|---|---|---|
| | $R_1$ | $R_2$ | $R_3$ | LM | Mod1 | Mod2 |
| 180 | H | H | H | S1 | G | E |
| 181 | H | H | OH | S1 | G | C |
| 182 | H | $CH_3$ | H | S1 | G | M |
| 183 | H | $CH_3$ | OH | S1 | G | J |
| 184 | $CH_3$ | H | H | S2 | G | E |
| 185 | $CH_3$ | H | OH | S2 | G | C |
| 186 | $CH_3$ | $CH_3$ | H | S2 | G | M |
| 187 | $CH_3$ | $CH_3$ | OH | S2 | G | J |

TABLE 3M

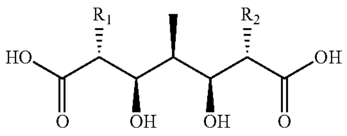

| | | | Modules | | |
|---|---|---|---|---|---|
| | $R_1$ | $R_2$ | LM | Mod1 | Mod2 |
| 188 | H | H | S1 | G | B |
| 189 | H | $CH_3$ | S1 | G | I |
| 190 | $CH_3$ | H | S2 | G | B |
| 191 | $CH_3$ | $CH_3$ | S2 | G | I |

TABLE 3N

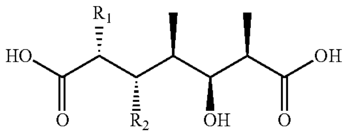

| | | | Modules | | |
|---|---|---|---|---|---|
| | $R_1$ | $R_2$ | LM | Mod1 | Mod2 |
| 192 | H | H | S1 | L | G |
| 193 | H | OH | S1 | H | G |
| 194 | $CH_3$ | H | S2 | L | G |
| 195 | $CH_3$ | OH | S2 | H | G |

TABLE 3O

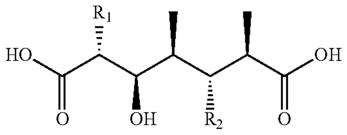

| | | | Modules | | |
|---|---|---|---|---|---|
| | $R_1$ | $R_2$ | LM | Mod1 | Mod2 |
| 196 | H | H | S1 | G | L |
| 197 | H | OH | S1 | G | H |
| 198 | $CH_3$ | H | S2 | G | L |
| 199 | $CH_3$ | OH | S2 | G | H |

TABLE 3P

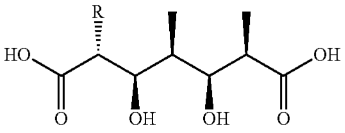

| | | Modules | | |
|---|---|---|---|---|
| | R | LM | Mod1 | Mod2 |
| 200 | H | S1 | G | G |
| 201 | $CH_3$ | S2 | G | G |

TABLE 3Q

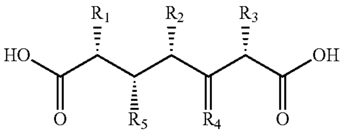

| | $R_1$ | $R_2$ | $R_3$ | $R_4$ | $R_5$ | Modules | | |
|---|---|---|---|---|---|---|---|---|
| | | | | | | LM | Mod1 | Mod2 |
| 202 | H | H | H | O | H | S1 | E | A |
| 203 | H | H | H | O | OH | S1 | C | A |
| 204 | H | H | $CH_3$ | O | H | S1 | E | F |
| 205 | H | H | $CH_3$ | O | OH | S1 | C | F |
| 206 | H | H | $(CH_2)_3$ | O | H | S1 | E | O |
| 207 | H | H | $(CH_2)_3$ | O | OH | S1 | C | O |
| 208 | H | H | $CH_2CH_3$ | O | H | S1 | E | P |
| 209 | H | H | $CH_2CH_3$ | O | OH | S1 | C | P |
| 210 | H | $CH_3$ | H | O | H | S1 | M | A |
| 211 | H | $CH_3$ | H | O | OH | S1 | J | A |
| 212 | H | $CH_3$ | $CH_3$ | O | H | S1 | M | F |
| 213 | H | $CH_3$ | $CH_2$ | O | OH | S1 | J | F |
| 214 | H | $CH_3$ | $(CH_2)_3$ | O | H | S1 | M | O |
| 215 | H | $CH_3$ | $(CH_2)_3$ | O | OH | S1 | J | O |
| 216 | H | $CH_3$ | $CH_2CH_3$ | O | H | S1 | M | P |
| 217 | H | $CH_3$ | $CH_2CH_3$ | O | OH | S1 | J | P |
| 218 | H | H | H | $CH_2$ | H | S1 | E | N |
| 219 | H | H | H | $CH_2$ | OH | S1 | C | N |
| 220 | H | $CH_3$ | H | $CH_2$ | H | S1 | M | N |
| 221 | H | $CH_3$ | H | $CH_2$ | OH | S1 | J | N |
| 222 | H | H | H | O | H | S2 | E | A |
| 223 | $CH_3$ | H | H | O | OH | S2 | C | A |
| 224 | $CH_3$ | H | $CH_3$ | O | H | S2 | E | F |
| 225 | $CH_3$ | H | $CH_2$ | O | OH | S2 | C | F |
| 226 | $CH_3$ | H | $(CH_2)_3$ | O | H | S2 | E | O |
| 227 | $CH_3$ | H | $(CH_2)_3$ | O | OH | S2 | C | O |
| 228 | $CH_3$ | H | $CH_2CH_3$ | O | H | S2 | E | P |
| 229 | $CH_3$ | H | $CH_2CH_3$ | O | OH | S2 | C | P |
| 230 | $CH_3$ | $CH_3$ | H | O | H | S2 | M | A |
| 231 | $CH_3$ | $CH_3$ | H | O | OH | S2 | J | A |
| 232 | $CH_3$ | $CH_3$ | $CH_3$ | O | H | S2 | M | F |
| 233 | $CH_3$ | $CH_3$ | $CH_3$ | O | OH | S2 | J | F |
| 234 | $CH_3$ | $CH_3$ | $(CH_2)_3$ | O | H | S2 | M | O |
| 235 | $CH_3$ | $CH_3$ | $(CH_2)_3$ | O | OH | S2 | J | O |
| 236 | $CH_3$ | $CH_3$ | $CH_2CH_3$ | O | H | S2 | M | P |
| 237 | $CH_3$ | $CH_3$ | $CH_2CH_3$ | O | OH | S2 | J | P |
| 238 | $CH_3$ | H | H | $CH_2$ | H | S2 | E | N |
| 239 | $CH_3$ | H | H | $CH_2$ | OH | S2 | C | N |
| 240 | $CH_3$ | $CH_3$ | H | $CH_2$ | H | S2 | M | N |
| 241 | $CH_3$ | $CH_3$ | H | $CH_2$ | OH | S2 | J | N |

TABLE 3R

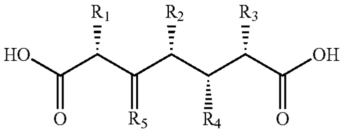

| | $R_1$ | $R_2$ | $R_3$ | $R_4$ | $R_5$ | Modules | | |
|---|---|---|---|---|---|---|---|---|
| | | | | | | LM | Mod1 | Mod2 |
| 242 | H | H | H | H | O | S1 | A | E |
| 243 | H | H | H | OH | O | S1 | A | C |
| 244 | H | H | $CH_3$ | H | O | S1 | A | M |
| 245 | H | H | $CH_3$ | OH | O | S1 | A | J |
| 246 | H | $CH_3$ | H | H | O | S1 | F | E |
| 247 | H | $CH_3$ | H | OH | O | S1 | F | C |
| 248 | H | $CH_3$ | $CH_3$ | H | O | S1 | F | M |
| 249 | H | $CH_3$ | $CH_3$ | OH | O | S1 | F | J |
| 250 | H | $(CH_2)_3$ | H | H | O | S1 | O | E |
| 251 | H | $(CH_2)_3$ | H | OH | O | S1 | O | C |
| 252 | H | $(CH_2)_3$ | $CH_3$ | H | O | S1 | O | M |
| 253 | H | $(CH_2)_3$ | $CH_3$ | OH | O | S1 | O | J |

TABLE 3R-continued

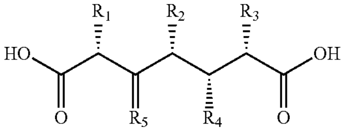

| | $R_1$ | $R_2$ | $R_3$ | $R_4$ | $R_5$ | Modules | | |
|---|---|---|---|---|---|---|---|---|
| | | | | | | LM | Mod1 | Mod2 |
| 254 | H | $CH_2CH_3$ | H | H | O | S1 | P | E |
| 255 | H | $CH_2CH_3$ | H | OH | O | S1 | P | C |
| 256 | H | $CH_2CH_3$ | $CH_3$ | H | O | S1 | P | M |
| 257 | H | $CH_2CH_3$ | $CH_3$ | OH | O | S1 | P | J |
| 258 | H | H | H | H | $CH_2$ | S1 | N | E |
| 259 | H | H | H | OH | $CH_2$ | S1 | N | C |
| 260 | H | H | $CH_3$ | H | $CH_2$ | S1 | N | M |
| 261 | H | H | $CH_3$ | OH | $CH_2$ | S1 | N | J |
| 262 | $CH_3$ | H | H | H | O | S2 | A | E |
| 263 | $CH_3$ | H | H | OH | O | S2 | A | C |
| 264 | $CH_3$ | H | $CH_3$ | H | O | S2 | A | M |
| 265 | $CH_3$ | H | $CH_3$ | OH | O | S2 | A | J |
| 266 | $CH_3$ | $CH_3$ | H | H | O | S2 | F | E |
| 267 | $CH_3$ | $CH_3$ | H | OH | O | S2 | F | C |
| 268 | $CH_3$ | $CH_3$ | $CH_3$ | H | O | S2 | F | M |
| 269 | $CH_3$ | $CH_3$ | $CH_3$ | OH | O | S2 | F | J |
| 270 | $CH_3$ | $(CH_2)_3$ | H | H | O | S2 | O | E |
| 271 | $CH_3$ | $(CH_2)_3$ | H | OH | O | S2 | O | C |
| 272 | $CH_3$ | $(CH_2)_3$ | $CH_3$ | H | O | S2 | O | M |
| 273 | $CH_3$ | $(CH_2)_3$ | $CH_3$ | OH | O | S2 | O | J |
| 274 | $CH_3$ | $CH_2CH_3$ | H | H | O | S2 | P | E |
| 275 | $CH_3$ | $CH_2CH_3$ | H | OH | O | S2 | P | C |
| 276 | $CH_3$ | $CH_2CH_3$ | $CH_3$ | H | O | S2 | P | M |
| 277 | $CH_3$ | $CH_2CH_3$ | $CH_3$ | OH | O | S2 | P | J |
| 278 | $CH_3$ | H | H | H | $CH_2$ | S2 | N | E |
| 279 | $CH_3$ | H | H | OH | $CH_2$ | S2 | N | C |
| 280 | $CH_3$ | H | $CH_3$ | H | $CH_2$ | S2 | N | M |
| 281 | $CH_3$ | H | $CH_3$ | OH | $CH_2$ | S2 | N | J |

TABLE 3S

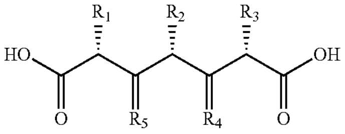

| | $R_1$ | $R_2$ | $R_3$ | $R_4$ | $R_5$ | Modules | | |
|---|---|---|---|---|---|---|---|---|
| | | | | | | LM | Mod1 | Mod2 |
| 282 | H | H | H | O | O | S1 | A | A |
| 283 | H | H | $CH_3$ | O | O | S1 | A | F |
| 284 | H | H | $(CH_2)_3$ | O | O | S1 | A | O |
| 285 | H | H | $CH_2CH_3$ | O | O | S1 | A | P |
| 286 | H | $CH_3$ | H | O | O | S1 | F | A |
| 287 | H | $CH_3$ | $CH_3$ | O | O | S1 | F | F |
| 288 | H | $CH_3$ | $(CH_2)_3$ | O | O | S1 | F | O |
| 289 | H | $CH_3$ | $CH_2CH_3$ | O | O | S1 | F | P |
| 290 | H | $(CH_2)_3$ | H | O | O | S1 | O | A |
| 291 | H | $(CH_2)_3$ | $CH_3$ | O | O | S1 | O | F |
| 292 | H | $(CH_2)_3$ | $(CH_2)_3$ | O | O | S1 | O | O |
| 293 | H | $(CH_2)_3$ | $CH_2CH_3$ | O | O | S1 | O | P |
| 294 | H | $CH_2CH_3$ | H | O | O | S1 | P | A |
| 295 | H | $CH_2CH_3$ | $CH_3$ | O | O | S1 | P | F |
| 296 | H | $CH_2CH_3$ | $(CH_2)_3$ | O | O | S1 | P | O |
| 297 | H | $CH_2CH_3$ | $CH_2CH_3$ | O | O | S1 | P | P |
| 298 | H | H | H | $CH_2$ | O | S1 | A | N |
| 299 | H | $CH_3$ | H | $CH_2$ | O | S1 | F | N |
| 300 | H | $(CH_2)_3$ | H | $CH_2$ | O | S1 | O | N |
| 301 | H | $CH_2CH_3$ | H | $CH_2$ | O | S1 | P | N |
| 302 | H | H | H | $CH_2$ | $CH_2$ | S1 | N | N |
| 303 | H | H | H | O | $CH_2$ | S1 | N | A |
| 304 | H | H | $CH_3$ | O | $CH_2$ | S1 | N | F |
| 305 | H | H | $CH_2)_3$ | O | $CH_2$ | S1 | N | O |

TABLE 3S-continued

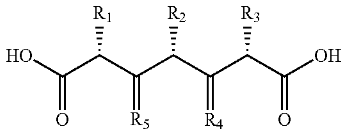

| | R1 | R2 | R3 | R4 | R5 | Modules LM | Mod1 | Mod2 |
|---|---|---|---|---|---|---|---|---|
| 306 | H | H | $CH_2CH_3$ | O | $CH_2$ | S1 | N | P |
| 307 | $CH_3$ | H | H | O | O | S2 | A | A |
| 308 | $CH_3$ | H | $CH_3$ | O | O | S2 | A | F |
| 309 | $CH_3$ | H | $(CH_2)_3$ | O | O | S2 | A | O |
| 310 | $CH_3$ | H | $CH_2CH_3$ | O | O | S2 | A | P |
| 311 | $CH_3$ | $CH_3$ | H | O | O | S2 | F | A |
| 312 | $CH_3$ | $CH_3$ | $CH_3$ | O | O | S2 | F | F |
| 313 | $CH_3$ | $CH_3$ | $(CH_2)_3$ | O | O | S2 | F | O |
| 314 | $CH_3$ | $CH_3$ | $CH_2CH_3$ | O | O | S2 | F | P |
| 315 | $CH_3$ | $(CH_2)_3$ | H | O | O | S2 | O | A |
| 316 | $CH_3$ | $(CH_2)_3$ | $CH_3$ | O | O | S2 | O | F |
| 317 | $CH_3$ | $(CH_2)_3$ | $(CH_2)_3$ | O | O | S2 | O | O |
| 318 | $CH_3$ | $(CH_2)_3$ | $CH_2CH_3$ | O | O | S2 | O | P |
| 319 | $CH_3$ | $CH_2CH_3$ | H | O | O | S2 | P | A |
| 320 | $CH_3$ | $CH_2CH_3$ | $CH_3$ | O | O | S2 | P | F |
| 321 | $CH_3$ | $CH_2CH_3$ | $(CH_2)_3$ | O | O | S2 | P | O |
| 322 | $CH_3$ | $CH_2CH_3$ | $CH_2CH_3$ | O | O | S2 | P | P |
| 323 | $CH_3$ | H | H | $CH_2$ | O | S2 | A | N |
| 324 | $CH_3$ | $CH_3$ | H | $CH_2$ | O | S2 | F | N |
| 325 | $CH_3$ | $(CH_2)_3$ | H | $CH_2$ | O | S2 | O | N |
| 326 | $CH_3$ | $CH_2CH_3$ | H | $CH_2$ | O | S2 | P | N |
| 327 | $CH_3$ | H | H | $CH_2$ | $CH_2$ | S2 | N | N |
| 328 | $CH_3$ | H | H | O | $CH_2$ | S2 | N | A |
| 329 | $CH_3$ | H | $CH_3$ | O | $CH_2$ | S2 | N | F |
| 330 | $CH_3$ | H | $(CH_2)_3$ | O | $CH_2$ | S2 | N | O |
| 331 | $CH_3$ | H | $CH_2CH_3$ | O | $CH_2$ | S2 | N | P |

TABLE 3T

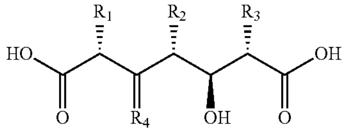

| | R1 | R2 | R3 | R4 | Modules LM | Mod1 | Mod2 |
|---|---|---|---|---|---|---|---|
| 332 | H | H | H | O | S1 | A | B |
| 333 | H | H | $CH_3$ | O | S1 | A | I |
| 334 | H | $CH_3$ | H | O | S1 | F | B |
| 335 | H | $CH_3$ | $CH_3$ | O | S1 | F | I |
| 336 | H | $(CH_2)_3$ | H | O | S1 | O | B |
| 337 | H | $(CH_2)_3$ | $CH_3$ | O | S1 | O | I |
| 338 | H | $CH_2CH_3$ | H | O | S1 | P | B |
| 339 | H | $CH_2CH_3$ | $CH_3$ | O | S1 | P | I |
| 340 | H | H | H | $CH_2$ | S1 | N | B |
| 341 | H | H | $CH_3$ | $CH_2$ | S1 | N | I |
| 342 | $CH_3$ | H | H | O | S2 | A | B |
| 343 | $CH_3$ | H | $CH_3$ | O | S2 | A | I |
| 344 | $CH_3$ | $CH_3$ | H | O | S2 | F | B |
| 345 | $CH_3$ | $CH_3$ | $CH_3$ | O | S2 | F | I |
| 346 | $CH_3$ | $(CH_2)_3$ | H | O | S2 | O | B |
| 347 | $CH_3$ | $(CH_2)_3$ | $CH_3$ | O | S2 | O | I |
| 348 | $CH_3$ | $CH_2CH_3$ | H | O | S2 | P | B |
| 349 | $CH_3$ | $CH_2CH_3$ | $CH_3$ | O | S2 | P | I |
| 350 | $CH_3$ | H | H | $CH_2$ | S2 | N | B |
| 351 | $CH_3$ | H | $CH_3$ | $CH_2$ | S2 | N | I |

TABLE 3U

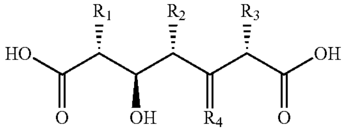

| | R1 | R2 | R3 | R4 | Modules LM | Mod1 | Mod2 |
|---|---|---|---|---|---|---|---|
| 352 | H | H | H | O | S1 | B | A |
| 353 | H | H | $CH_3$ | O | S1 | B | F |
| 354 | H | H | $(CH_2)_3$ | O | S1 | B | O |
| 355 | H | H | $CH_2CH_3$ | O | S1 | B | P |
| 356 | H | H | H | $CH_2$ | S1 | B | N |
| 357 | H | $CH_3$ | H | O | S1 | I | A |
| 358 | H | $CH_3$ | $CH_3$ | O | S1 | I | F |
| 359 | H | $CH_3$ | $(CH_2)_3$ | O | S1 | I | O |
| 360 | H | $CH_3$ | $CH_2CH_3$ | O | S1 | I | P |
| 351 | H | $CH_3$ | H | $CH_2$ | S1 | I | N |
| 362 | $CH_3$ | H | H | O | S2 | B | A |
| 363 | $CH_3$ | H | $CH_3$ | O | S2 | B | F |
| 364 | $CH_3$ | H | $(CH_2)_3$ | O | S2 | B | O |
| 365 | $CH_3$ | H | $CH_2CH_3$ | O | S2 | B | P |
| 366 | $CH_3$ | H | H | $CH_2$ | S2 | B | N |
| 367 | $CH_3$ | $CH_3$ | H | O | S2 | I | A |
| 368 | $CH_3$ | $CH_3$ | $CH_3$ | O | S2 | I | F |
| 369 | $CH_3$ | $CH_3$ | $(CH_2)_3$ | O | S2 | I | O |
| 370 | $CH_3$ | $CH_3$ | $CH_2CH_3$ | O | S2 | I | P |
| 371 | $CH_3$ | $CH_3$ | H | $CH_2$ | S2 | I | N |

TABLE 3V

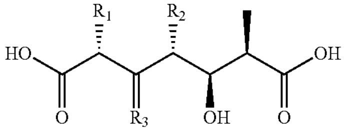

| | R1 | R2 | R3 | Modules LM | Mod1 | Mod2 |
|---|---|---|---|---|---|---|
| 372 | H | H | O | S1 | A | G |
| 373 | H | $CH_3$ | O | S1 | F | G |
| 374 | H | $(CH_2)_3$ | O | S1 | O | G |
| 375 | H | $CH_2CH_3$ | O | S1 | P | G |
| 376 | H | H | $CH_2$ | S1 | N | G |
| 377 | $CH_3$ | H | O | S2 | A | G |
| 378 | $CH_3$ | $CH_3$ | O | S2 | F | G |
| 379 | $CH_3$ | $(CH_2)_3$ | O | S2 | O | G |
| 380 | $CH_3$ | $CH_2CH_3$ | O | S2 | P | G |
| 381 | $CH_3$ | H | $CH_2$ | S2 | N | G |

TABLE 3W

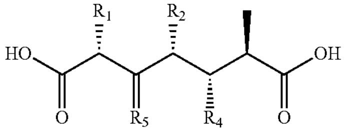

| | R1 | R2 | R3 | R4 | R5 | Modules LM | Mod1 | Mod2 |
|---|---|---|---|---|---|---|---|---|
| 382 | H | H | $CH_3$ | H | O | S1 | A | L |
| 383 | H | H | $CH_3$ | OH | O | S1 | A | H |
| 384 | H | H | $CH_3$ | H | $CH_2$ | S1 | N | L |
| 385 | H | H | $CH_3$ | OH | $CH_2$ | S1 | N | H |
| 386 | H | $CH_3$ | $CH_3$ | H | O | S1 | F | L |
| 387 | H | $CH_3$ | $CH_3$ | OH | O | S1 | F | H |

TABLE 3W-continued

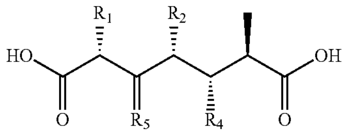

| | $R_1$ | $R_2$ | $R_3$ | $R_4$ | $R_5$ | Modules LM | Mod1 | Mod2 |
|---|---|---|---|---|---|---|---|---|
| 388 | H | $(CH_2)_3$ | $CH_3$ | H | O | S1 | O | L |
| 389 | H | $(CH_2)_3$ | $CH_3$ | OH | O | S1 | O | H |
| 390 | H | $CH_2CH_3$ | $CH_3$ | H | O | S1 | P | L |
| 391 | H | $CH_2CH_3$ | $CH_3$ | OH | O | S1 | P | H |
| 392 | $CH_3$ | H | $CH_3$ | H | O | S2 | A | L |
| 393 | $CH_3$ | H | $CH_3$ | OH | O | S2 | A | H |
| 394 | $CH_3$ | H | $CH_3$ | H | $CH_2$ | S2 | N | L |
| 395 | $CH_3$ | H | $CH_3$ | OH | $CH_2$ | S2 | N | H |
| 396 | $CH_3$ | $CH_3$ | $CH_3$ | H | O | S2 | F | L |
| 397 | $CH_3$ | $CH_3$ | $CH_3$ | OH | O | S2 | F | H |
| 398 | $CH_3$ | $(CH_2)_3$ | $CH_3$ | H | O | S2 | O | L |
| 399 | $CH_3$ | $(CH_2)_3$ | $CH_3$ | OH | O | S2 | O | H |
| 400 | $CH_3$ | $CH_2CH_3$ | $CH_3$ | H | O | S2 | P | L |
| 401 | $CH_3$ | $CH_2CH_3$ | $CH_3$ | OH | O | S2 | P | H |

TABLE 3X

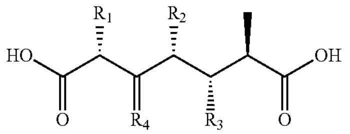

| | $R_1$ | $R_2$ | $R_3$ | $R_4$ | Modules LM | Mod1 | Mod2 |
|---|---|---|---|---|---|---|---|
| 382 | H | H | H | O | S1 | A | L |
| 383 | H | H | OH | O | S1 | A | H |
| 384 | H | H | H | $CH_2$ | S1 | N | L |
| 385 | H | H | OH | $CH_2$ | S1 | N | H |
| 386 | H | $CH_3$ | H | O | S1 | F | L |
| 387 | H | $CH_3$ | OH | O | S1 | F | H |
| 388 | H | $(CH_2)_3$ | H | O | S1 | O | L |
| 389 | H | $(CH_2)_3$ | OH | O | S1 | O | H |
| 390 | H | $CH_2CH_3$ | H | O | S1 | P | L |
| 391 | H | $CH_2CH_3$ | OH | O | S1 | P | H |
| 392 | $CH_3$ | H | H | O | S2 | A | L |
| 393 | $CH_3$ | H | OH | O | S2 | A | H |
| 394 | $CH_3$ | H | H | $CH_2$ | S2 | N | L |
| 395 | $CH_3$ | H | OH | $CH_2$ | S2 | N | H |
| 396 | $CH_3$ | $CH_3$ | H | O | S2 | F | L |
| 397 | $CH_3$ | $CH_3$ | OH | O | S2 | F | H |
| 398 | $CH_3$ | $(CH_2)_3$ | H | O | S2 | O | L |
| 399 | $CH_3$ | $(CH_2)_3$ | OH | O | S2 | O | H |
| 400 | $CH_3$ | $CH_2CH_3$ | H | O | S2 | P | L |
| 401 | $CH_3$ | $CH_2CH_3$ | OH | O | S2 | P | H |

TABLE 3Y

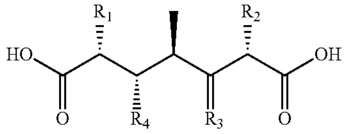

| | $R_1$ | $R_2$ | $R_3$ | $R_4$ | Modules LM | Mod1 | Mod2 |
|---|---|---|---|---|---|---|---|
| 402 | H | H | O | H | S1 | L | A |
| 403 | H | $CH_3$ | O | H | S1 | L | F |

TABLE 3Y-continued

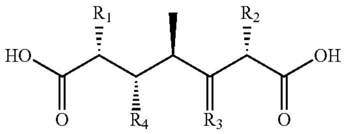

| | $R_1$ | $R_2$ | $R_3$ | $R_4$ | Modules LM | Mod1 | Mod2 |
|---|---|---|---|---|---|---|---|
| 404 | H | $(CH_2)_3$ | O | H | S1 | L | O |
| 405 | H | $CH_2CH_3$ | O | H | S1 | L | P |
| 406 | H | H | $CH_2$ | H | S1 | L | N |
| 407 | H | H | O | OH | S1 | H | A |
| 408 | H | $CH_3$ | O | OH | S1 | H | F |
| 409 | H | $(CH_2)_3$ | O | OH | S1 | H | O |
| 410 | H | $CH_2CH_3$ | O | OH | S1 | H | P |
| 411 | H | H | $CH_2$ | OH | S1 | H | N |
| 412 | $CH_3$ | H | O | H | S2 | L | A |
| 413 | $CH_3$ | $CH_3$ | O | H | S2 | L | F |
| 414 | $CH_3$ | $(CH_2)_3$ | O | H | S2 | L | O |
| 415 | $CH_3$ | $CH_2CH_3$ | O | H | S2 | L | P |
| 416 | $CH_3$ | H | $CH_2$ | H | S2 | L | N |
| 417 | $CH_3$ | H | O | OH | S2 | H | A |
| 418 | $CH_3$ | $CH_3$ | O | OH | S2 | H | F |
| 419 | $CH_3$ | $(CH_2)_3$ | O | OH | S2 | H | O |
| 420 | $CH_3$ | $CH_2CH_3$ | O | OH | S2 | H | P |
| 421 | $CH_3$ | H | $CH_2$ | OH | S2 | H | N |

TABLE 3Z

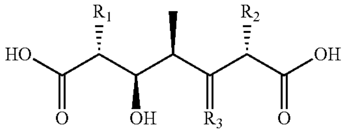

| | $R_1$ | $R_2$ | $R_3$ | Modules LM | Mod1 | Mod2 |
|---|---|---|---|---|---|---|
| 423 | H | H | O | S1 | G | A |
| 424 | H | $CH_3$ | O | S1 | G | F |
| 425 | H | $(CH_2)_3$ | O | S1 | G | O |
| 426 | H | $CH_2CH_3$ | O | S1 | G | P |
| 427 | H | H | $CH_2$ | S1 | G | N |
| 428 | $CH_3$ | H | O | S2 | G | A |
| 429 | $CH_3$ | $CH_3$ | O | S2 | G | F |
| 430 | $CH_3$ | $(CH_2)_3$ | O | S2 | G | O |
| 431 | $CH_3$ | $CH_2CH_3$ | O | S2 | G | P |
| 432 | $CH_3$ | H | $CH_2$ | S2 | G | N |

TABLE 3AA

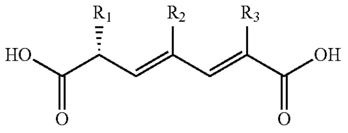

| | $R_1$ | $R_2$ | $R_3$ | Modules LM | Mod1 | Mod2 |
|---|---|---|---|---|---|---|
| 433 | H | H | H | S1 | D | D |
| 434 | H | H | $CH_3$ | S1 | D | K |
| 435 | H | $CH_3$ | H | S1 | K | D |
| 436 | H | $CH_3$ | $CH_3$ | S1 | K | K |
| 437 | $CH_3$ | H | H | S2 | D | D |
| 438 | $CH_3$ | H | $CH_3$ | S2 | D | K |
| 439 | $CH_3$ | $CH_3$ | H | S2 | K | D |
| 440 | $CH_3$ | $CH_3$ | $CH_3$ | S2 | K | K |

TABLE 3BB

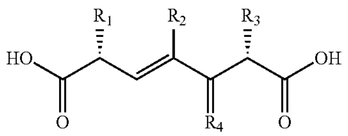

| | $R_1$ | $R_2$ | $R_3$ | $R_4$ | Modules LM | Mod1 | Mod2 |
|---|---|---|---|---|---|---|---|
| 441 | H | H | H | O | S1 | D | A |
| 442 | H | H | $CH_3$ | O | S1 | D | F |
| 443 | H | H | $(CH_2)_3$ | O | S1 | D | O |
| 444 | H | H | $CH_2CH_3$ | O | S1 | D | P |
| 445 | H | $CH_3$ | H | O | S1 | K | A |
| 446 | H | $CH_3$ | $CH_3$ | O | S1 | K | F |
| 447 | H | $CH_3$ | $(CH_2)_3$ | O | S1 | K | O |
| 448 | H | $CH_3$ | $CH_2CH_3$ | O | S1 | K | P |
| 449 | H | H | H | $CH_2$ | S1 | D | N |
| 450 | H | $CH_3$ | H | $CH_2$ | S1 | K | N |
| 451 | $CH_3$ | H | H | O | S2 | D | A |
| 452 | $CH_3$ | H | $CH_3$ | O | S2 | D | F |
| 453 | $CH_3$ | H | $(CH_2)_3$ | O | S2 | D | O |
| 454 | $CH_3$ | H | $CH_2CH_3$ | O | S2 | D | P |
| 455 | $CH_3$ | $CH_3$ | H | O | S2 | K | A |
| 456 | $CH_3$ | $CH_3$ | $CH_3$ | O | S2 | K | F |
| 457 | $CH_3$ | $CH_3$ | $(CH_2)_3$ | O | S2 | K | O |
| 458 | $CH_3$ | $CH_3$ | $CH_2CH_3$ | O | S2 | K | P |
| 459 | $CH_3$ | H | H | $CH_2$ | S2 | D | N |
| 460 | $CH_3$ | $CH_3$ | H | $CH_2$ | S2 | K | N |

TABLE 3CC

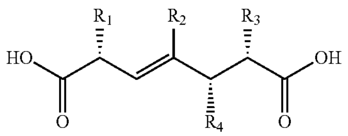

| | $R_1$ | $R_2$ | $R_3$ | $R_4$ | Modules LM | Mod1 | Mod2 |
|---|---|---|---|---|---|---|---|
| 461 | H | H | H | H | S1 | D | E |
| 462 | H | H | H | OH | S1 | D | C |
| 463 | H | H | $CH_3$ | H | S1 | D | M |
| 464 | H | H | $CH_3$ | OH | S1 | D | J |
| 465 | H | $CH_3$ | H | H | S1 | K | E |
| 466 | H | $CH_3$ | H | OH | S1 | K | C |
| 467 | H | $CH_3$ | $CH_3$ | H | S1 | K | M |
| 468 | H | $CH_3$ | $CH_3$ | OH | S1 | K | J |
| 469 | $CH_3$ | H | H | H | S2 | D | E |
| 470 | $CH_3$ | H | H | OH | S2 | D | C |
| 471 | $CH_3$ | H | $CH_3$ | H | S2 | D | M |
| 472 | $CH_3$ | H | $CH_3$ | OH | S2 | D | J |
| 473 | $CH_3$ | $CH_3$ | H | H | S2 | K | E |
| 474 | $CH_3$ | $CH_3$ | H | OH | S2 | K | C |
| 475 | $CH_3$ | $CH_3$ | $CH_3$ | H | S2 | K | M |
| 476 | $CH_3$ | $CH_3$ | $CH_3$ | OH | S2 | K | J |

TABLE 3DD

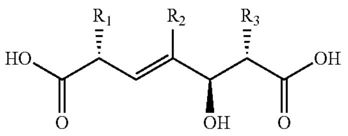

| | $R_1$ | $R_2$ | $R_3$ | Modules LM | Mod1 | Mod2 |
|---|---|---|---|---|---|---|
| 477 | H | H | H | S1 | D | B |
| 478 | H | H | $CH_3$ | S1 | D | I |
| 479 | H | $CH_3$ | H | S1 | K | B |
| 480 | H | $CH_3$ | $CH_3$ | S1 | K | I |
| 481 | $CH_3$ | H | H | S2 | D | B |
| 482 | $CH_3$ | H | $CH_3$ | S2 | D | I |
| 483 | $CH_3$ | $CH_3$ | H | S2 | K | B |
| 484 | $CH_3$ | $CH_3$ | $CH_3$ | S2 | K | I |

TABLE 3EE

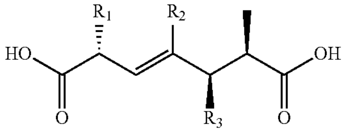

| | $R_1$ | $R_2$ | $R_3$ | Modules LM | Mod1 | Mod2 |
|---|---|---|---|---|---|---|
| 485 | H | H | H | S1 | D | L |
| 486 | H | H | OH | S1 | D | G |
| 487 | H | $CH_3$ | H | S1 | K | L |
| 488 | H | $CH_3$ | OH | S1 | K | G |
| 489 | $CH_3$ | H | H | S2 | D | L |
| 490 | $CH_3$ | H | OH | S2 | D | G |
| 491 | $CH_3$ | $CH_3$ | H | S2 | K | L |
| 492 | $CH_3$ | $CH_3$ | OH | S2 | K | G |

TABLE 3FF

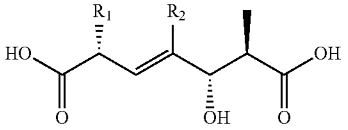

| | $R_1$ | $R_2$ | Modules LM | Mod1 | Mod2 |
|---|---|---|---|---|---|
| 493 | H | H | S1 | D | H |
| 494 | H | $CH_3$ | S1 | K | H |
| 495 | $CH_3$ | H | S2 | D | H |
| 496 | $CH_3$ | $CH_3$ | S2 | K | H |

TABLE 3GG

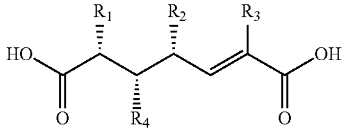

| | | | | | Modules | | |
|---|---|---|---|---|---|---|---|
| | $R_1$ | $R_2$ | $R_3$ | $R_4$ | LM | Mod1 | Mod2 |
| 497 | H | H | H | H | S1 | E | D |
| 498 | H | H | $CH_3$ | H | S1 | E | K |
| 499 | H | H | H | OH | S1 | C | D |
| 500 | H | H | $CH_3$ | OH | S1 | C | K |
| 501 | H | $CH_3$ | H | H | S1 | M | D |
| 502 | H | $CH_3$ | $CH_3$ | H | S1 | M | K |
| 503 | H | $CH_3$ | H | OH | S1 | J | D |
| 504 | H | $CH_3$ | $CH_3$ | OH | S1 | J | K |
| 505 | $CH_3$ | H | H | H | S2 | E | D |
| 506 | $CH_3$ | H | $CH_3$ | H | S2 | E | K |
| 507 | $CH_3$ | H | H | OH | S2 | C | D |
| 508 | $CH_3$ | H | $CH_3$ | OH | S2 | C | K |
| 509 | $CH_3$ | $CH_3$ | H | H | S2 | M | D |
| 510 | $CH_3$ | $CH_3$ | $CH_3$ | H | S2 | M | K |
| 511 | $CH_3$ | $CH_3$ | H | OH | S2 | J | D |
| 512 | $CH_3$ | CH, | $CH_3$ | OH | S2 | J | K |

TABLE 3HH

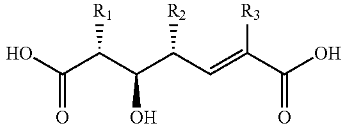

| | | | | Modules | | |
|---|---|---|---|---|---|---|
| | $R_1$ | $R_2$ | $R_3$ | LM | Mod1 | Mod2 |
| 513 | H | H | H | S1 | B | D |
| 514 | H | H | $CH_3$ | S1 | B | K |
| 515 | H | $CH_3$ | H | S1 | I | D |
| 516 | H | $CH_3$ | $CH_3$ | S1 | I | K |
| 517 | $CH_3$ | H | H | S2 | B | D |
| 518 | $CH_3$ | H | $CH_3$ | S2 | B | K |
| 519 | $CH_3$ | $CH_3$ | H | S2 | I | D |
| 520 | $CH_3$ | $CH_3$ | $CH_3$ | S2 | I | K |

TABLE 3II

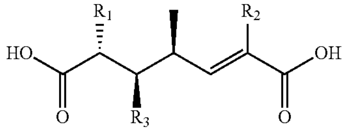

| | | | | Modules | | |
|---|---|---|---|---|---|---|
| | $R_1$ | $R_2$ | $R_3$ | LM | Mod1 | Mod2 |
| 521 | H | H | H | S1 | L | D |
| 522 | H | $CH_3$ | H | S1 | L | K |
| 523 | H | H | OH | S1 | G | D |
| 524 | H | $CH_3$ | OH | S1 | G | K |
| 525 | CH | H | H | S2 | L | D |
| 526 | $CH_3$ | $CH_3$ | H | S2 | L | K |
| 527 | $CH_3$ | H | OH | S2 | G | D |
| 528 | $CH_3$ | $CH_3$ | OH | S2 | G | K |

TABLE 3JJ

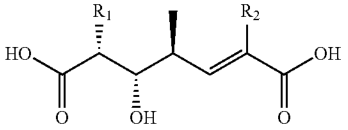

| | | | Modules | | |
|---|---|---|---|---|---|
| | $R_1$ | $R_2$ | LM | Mod1 | Mod2 |
| 529 | H | H | S1 | H | D |
| 530 | H | $CH_3$ | S1 | H | K |
| 531 | $CH_3$ | H | S2 | H | D |
| 532 | $CH_3$ | $CH_3$ | S2 | H | K |

TABLE 3KK

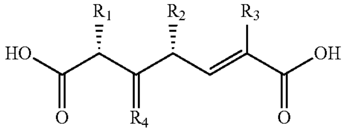

| | | | | | Modules | | |
|---|---|---|---|---|---|---|---|
| | $R_1$ | $R_2$ | $R_3$ | $R_4$ | LM | Mod1 | Mod2 |
| 533 | H | H | H | O | S1 | A | D |
| 534 | H | H | $CH_3$ | O | S1 | A | K |
| 535 | H | H | H | $CH_2$ | S1 | N | D |
| 536 | H | H | $CH_3$ | $CH_2$ | S1 | N | K |
| 537 | H | $CH_3$ | H | O | S1 | F | D |
| 538 | H | $CH_3$ | $CH_3$ | O | S1 | F | K |
| 539 | H | $(CH_2)_3$ | H | O | S1 | O | D |
| 540 | H | $(CH_2)_3$ | $CH_3$ | O | S1 | O | K |
| 541 | H | $CH_2CH_3$ | H | O | S1 | P | D |
| 542 | H | $CH_2CH_3$ | $CH_3$ | O | S1 | P | K |
| 543 | $CH_3$ | H | H | O | S2 | A | D |
| 544 | $CH_3$ | H | $CH_3$ | O | S2 | A | K |
| 545 | $CH_3$ | H | H | $CH_2$ | S2 | N | D |
| 546 | $CH_3$ | H | $CH_3$ | $CH_2$ | S2 | N | K |
| 547 | $CH_3$ | $CH_3$ | H | O | S2 | F | D |
| 548 | $CH_3$ | $CH_3$ | $CH_3$ | O | S2 | F | K |
| 549 | $CH_3$ | $(CH_2)_3$ | H | O | S2 | O | D |
| 550 | $CH_3$ | $(CH_2)_3$ | $CH_3$ | O | S2 | O | K |
| 551 | $CH_3$ | $CH_2CH_3$ | H | O | S2 | P | D |
| 552 | $CH_3$ | $CH_2CH_3$ | $CH_3$ | O | S2 | P | K |

Longer Chain Diacids from Polyketide Synthases

The polyketide backbone will increase by two carbon atoms for each module employed in the biosynthesis. Employing the starter and extender molecules shown in FIG. 2, the number of possible diacids that can be produced by hybrid PKSs is shown in Table 4. Each class would contain only a single symmetric molecule (the fully reduced diacid); all others would be asymmetric

TABLE 4

Number of polyketide possible from modules shown in FIG. 2.

| General Class | Number of Extender Modules | Number of Carbons in Polyketide Chain | Number of Possible Molecules |
|---|---|---|---|
| Diketide | 1 | 5 | 32 |
| Triketide | 2 | 7 | 512 |
| Tetraketide | 3 | 9 | 8,192 |
| Pentaketide | 4 | 11 | 262,144 |

The invention having been described, the following examples are offered to illustrate the subject invention by way of illustration, not by way of limitation.

Example 1

Production of Diacids

One can construct polyketide synthases and introduce these synthases into the bacterium *Escherichia coli* (or another readily engineered host) so that this well-known microorganism can produce from a renewable sugar (e.g., glucose) source any number of diacids that could replace those made from oil or other non-renewable feedstocks.

One can produce the following diacids: pentane-1,5-dioic acid; heptane-1,7-dioic acid; 2-methylpentane-1,5-dioic acid in *E. coli, S. cerevisiae* or *Streptomyces.*

Figure 5:
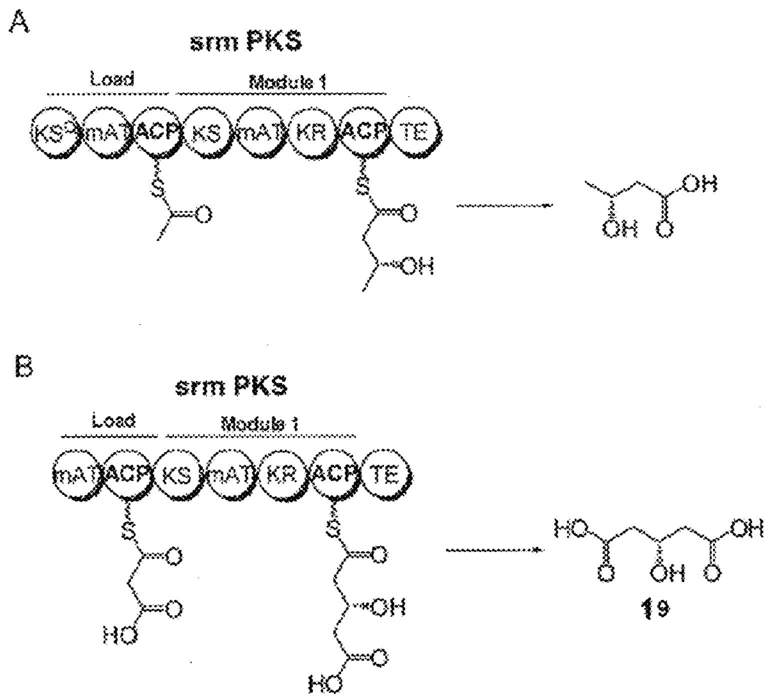
FIG. 5 shows the construction of a PKS to confirm production of a diacid. A. Loading domain and module 1 of srm PKS (Blue) is combined with a heterologous TE domain (black) to produce [8]. Construct in A is re-engineered to remove functional $KS^{Q}$ domain to produce [9]. Abbreviations as in FIGS. 9 and 10.

The three compounds listed above require the construction of hybrid PKSs containing two "unnatural" junctions, as well as the removal or inactivation of the $KS^Q$ segment of the loading domain. A "natural" PKS can be modified to produce a diacid. The DNA segment containing the loading domain and module 1 of the spiramycin (srm) PKS is cloned into the *E. coli* vector pPRO18 (S. K. Lee, J. D. Keasling, *Appl Environ Microbiol* 71, 6856 (2005); hereby incorporated by reference) or pET28B and is introduced the DNA segment containing the TE domain from the ery PKS or the monCII gene encoding a TE function from the monensin polyketide pathway (B. M. Harvey et al., *Chembiochem* 7, 1435 (2006); hereby incorporated by reference) downstream of module 1 as shown in FIG. 5A. Segments are joined using SLIC (sequence and ligase independent cloning) schemes so that "scarring" (altered sequences at the junction point) does not occur (M. Z. Li, S. J. Elledge, *Nat Methods* 4, 251 (2007); hereby incorporated by reference). This construction is confirmed correct by showing that the host (*E. coli*) produces (3-hydroxybutyrate) employing LCMS analysis against the authentic standard which can be obtained commercially. The construct shown in FIG. 5A is re-cloned or sub-cloned to eliminate all or most of the segment corresponding to the $KS^Q$ domain (or use site-directed mutagenesis of the active site of the decarboxylation function) in the same vector as shown in FIG. 5B, and test the various constructs for production of the diacid [19], following the procedure of El-Jaber et al. (N. El-Jaber et al., *J Nat Prod* 66, 722 (2003); hereby incorporated by reference) for isolation and purification. The structure is confirmed by NMR analysis. Alternately, besides the production of [19] in *E. coli*, the construct of FIG. 5A and the various constructs of FIG. 5B are sub-cloned into derivatives of the *Streptomyces* vectors pSET 152 (integrating) and pRJ446 (automously replicating) and introduced them into various *Streptomyces* hosts (e.g. *S. coelicolor, S. lividans, S. fradiae*) for production of [19] in these constructs. In addition, one can use loading domain-module 1 segments from other PKS systems (e.g. oligomycin, primaricin) to generate [19] (as the 3-stereoisomer) to demonstrate the production of the diacid, if necessary. These approaches should yield the expected diacid. The PKS genes described herein, or the hosts that carry them, are available from the American Type Culture Collection (ATCC) depository.

Example 2

Production of pentane-1,5,-dioic acid [7]

One can follow a similar experimental pathway (as described in Example 1) to produce [7]. Because there are no natural PKS systems that connect a malonate utilizing-loading domain to an extender module that contains both a malonate-specific AT domain (mAT) and the full set of reduction domains (DH, ER, KR) to yield β-methylene center (FIG. 10), a "hybrid" is to be constructed. The re-constructed loading domain from Example 1 that yields the diacid in a variety of genetic constructions is used. These include fusion to a DNA segment containing module 5 or module 6 from the nystatin PKS from *Streptomyces noursei* ATCC 11455 or module 3 from the oligomycin PKS from *Streptomyces avermitilis*, or addition of the DH and ER domains from a variety of modules to module 1 of the srm PKS to enable full reduction to produce the required β-methylene center. Alternatively, one can employ the segment containing the loading domain through the KS domain of module 1 from a single PKS fused to the AT-ACP segment of module 2. This keeps the cognate relationship between the loading domain ACP and the KS domain of module 1, as well as maintaining the proper intermodular spacing. A third approach is to employ the segment of the nystatin PKS encoding modules 5 and 6 directly wherein the KS domain of module 5 is removed or inactivated enabling module 5 to serve as a loading domain. (The presence of the reduction domains should not interfere with its use in subsequent condensation on module 1.) Each of these constructs is attached to the TE domain as described in Example 1, placed in the appropriate vector and host and then used to test for production of [7]. The PKS genes described herein, or the hosts that carry them are available from the ATCC depository.

Example 3

Production of heptane-1,7-dioic acid [10]

Figure 6:
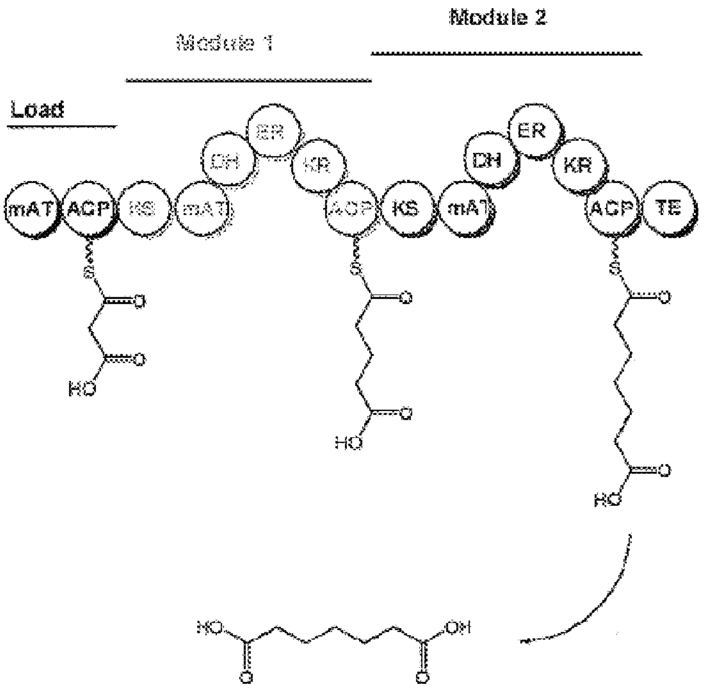
FIG. 6 shows a hybrid PKS consisting of an altered loading domain, module 1, module 2 and a TE domain to produce heotane-1,7-dioic acid. Abbreviations as in FIGS. 9 and 10.

Production of [8] requires the addition of a second extender module to produce a triketide-diacid. To the optimal construct required to produce [7] is added an additional module containing an mAT domain and a full set of reduction domains between module 1 and the TE domain to produce the hybrid PKS shown in FIG. 6.

Example 4

Production of 2-methylpentane-1,5-dioic acid [11]

Figure 7:
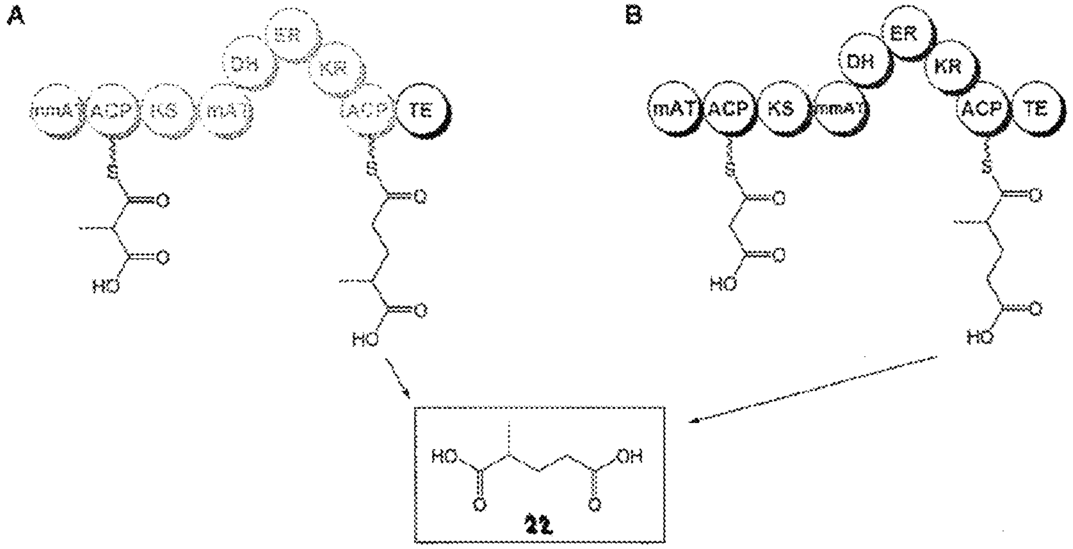
FIG. 7 shows hybrid PKSs consisting of an altered loading domain, module 1 and a TE domain to produce 2-methyl-1,5-pentanedioic acid. A. The loading domain contains a methylmalonyl-specific AT domain (mmAT). B. The extender domain contains an mmAT domain. All other abbreviations as in FIG. 9.

Two alternative strategies can be used to produce [22], as shown in FIG. 7. The hybrid PKS can employ a methylmalonyl-specific AT domain (mmAT) in either the loading domain (FIG. 7A) or in the extender domain (FIG. 7B). Both the loading domain and module 4 of the pik PKS (FIG. 5) contain mmAT domains (and result in the same chirality of the corresponding methyl side chain; the [S]-2-methyl- and [S]-3-methylpentane-1,5-dioic acids are identical). Opposite chirality can be obtained by choice of module. In *E. coli*, high levels of [2S]-methylmalonyl CoA can be produced from succinyl CoA by introduction of the gene mutA from *Propionibacterium shermanii* (L. C. Dayem et al., *Biochemistry* 41, 5193 (2002); hereby incorporated by reference). *E. coli* strains expressing mutA are well-known and are readily available.

Example 5

Production of pentane-1,5-dioic acid at 1 g/1

The titers of production of [7], and its counterpart n-butyric acid [6] that employ the same basis of construction and use both constructs is determined A large difference between production of n-butyric acid and [7] would suggest that either the modified loading domain does not give optimum utilization, or that the carboxyl group at the front end of the polyketide inhibits flux through the PKS. The secondary structure of the mRNA transcripts in the original design of the constructs is checked to rule this out as a basis for poor expression. A number of reconstructions of the loading domain can be tried to inactivate the $KS^Q$ domain and look for titer increases. In addition, one can mutagenize in vitro the PKS construct of the strain that produces [7], re-introduce the DNA into the host and test several hundred independent isolates for titer increases.

If the initial evaluation does not show significant differences in the titers of n-butyric acid and [7], the limitation of titer is due to factors involved with the expression of the PKS DNA in the host, turnover of the PKS proteins, or the supply of substrates. One can use an 'OMICS approach to understand the basis of the limitation (i.e., transcript, protein and metabolite analysis). Once the limitation is discovered, necessary steps can be taken to remedy it (e.g. change promoters, inactivate degradation enzymes, change hosts, eliminate side pathways, etc.)

Example 6

Production of Additional Diacids

Figure 8:
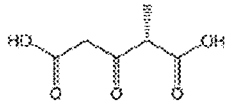
FIG. 8 shows di- and tri-ketide acids to be produced from PKS constructs showing modules required under each compound. All PKSs have altered loading domains and extender domains as shown. Abbreviations as in FIG. 9. (S) and (R) refer to the chirality of the methyl or OH groups formed from use of the corresponding module.
Figure 8:
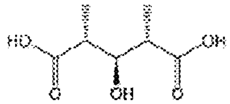
Figure 8:
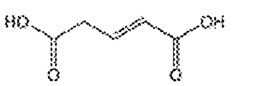
Figure 8:
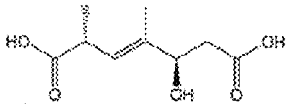
Figure 8:
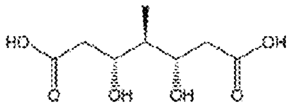
Figure 8:
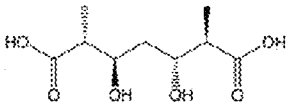

Greater than one dozen extender modules that yield structural different incorporated 2-carbon units in nascent polyketide chains are known. Variation comes from the side chain of the α-methyl carbon (H, [R]-methyl, [S]-methyl, [S]-ethyl, [S]-propylene, etc.) and the degree of reduction of the β-carbonyl (ketone, [R]-OH, [S]-OH, ene, methylene). Employing either malonyl CoA, or methylmalonyl CoA as the starter, more than two dozen diketide-diacids, and more than 250 triketide-diacids can be made. One can produce 6-10 diacids or triacids employing extender modules most readily available (e.g. where the module has been cloned previously and used in another application and can be re-used here). Compounds [10, 30, 37, 117, 165, 483], shown in FIG. 8, represent examples of molecules one can make and the modules required for their construction. Further examples of diketide-diacids and triketide-diacids are found taught in Tables 2A-F and Tables 3A-KK.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant polyketide synthase (PKS) capable of synthesizing a dicarboxylic acid (diacid), said PKS comprising a loading module containing a beta-keto acyl carrier protein synthase Q domain ($KS^Q$) lacking decarboxylase activity, one or more extender modules and a thioesterase (TE) domain.

2. The PKS of claim 1, wherein said diacid is pentane-1,5-dioic acid, and said PKS has a loading module that utilizes malonate and a single extender module that has a malonate-specific acyltransferase (AT) domain and a full set of reduction domains.

3. The PKS of claim 2, wherein the loading module is from spiromycin, the single extender module is module 5 or module 6 from nystatin PKS or module 3 from the oligomycin PKS, and the TE domain is from erythromycin PKS.

4. The PKS of claim 1, wherein said diacid is heptane-1,7-dioic acid; and said PKS has a loading module that utilizes malonate; a first and a second extender module, each of which has a malonate-specific acyltransferase (AT) domain; and a full set of reduction domains.

5. The PKS of claim 4, wherein the loading module is from spiromycin, the first extender module is module 5 or module 6 from nystatin PKS or module 3 from the oligomycin PKS, the second extender module is module 5 from the epothilone PKS, and the TE domain is from erythromycin PKS.

6. The PKS of claim 1, wherein said PKS comprises the loading module and module 1 of the spiramycin, oligomycin, or primaricin PKS; and the TE domain from erythromycin PKS or the TE domain encoded by the monCII gene; wherein the $KS^Q$ domain of the loading module is deleted or modified to inactivate the decarboxylase activity.

7. The PKS of claim 1, wherein the diacid comprises from 1 to 10 ketide units.

8. The PKS of claim 7, wherein the diacid comprises from 1 to 6 ketide units.

9. The PKS of claim 8, wherein the diacid comprises from 1 to 3 ketide units.

10. The PKS of claim 9, wherein the diacid is one described in Tables 2A-F and Tables 3A-KK.

11. A host cell comprising the PKS of claim 1.

12. The host cell of claim 11, wherein the host cell is a prokaryotic host cell.

13. The host cell of claim 12, wherein the prokaryotic host cell is an *E. coli* or a *Streptomyces* sp. cell.

14. The host cell of claim 11, wherein the host cell is a yeast host cell.

* * * * *